US010314578B2

(12) United States Patent
Leimbach et al.

(10) Patent No.: US 10,314,578 B2
(45) Date of Patent: Jun. 11, 2019

(54) BATTERY DRAIN CIRCUIT FOR SURGICAL INSTRUMENT

(71) Applicant: Ethicon Endo-Surgery, LLC, Guaynabo, PR (US)

(72) Inventors: Richard L Leimbach, Cincinnati, OH (US); Shane Adams, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 629 days.

(21) Appl. No.: 14/868,747

(22) Filed: Sep. 29, 2015

(65) Prior Publication Data

US 2017/0086826 A1 Mar. 30, 2017

(51) Int. Cl.
*H01M 10/42* (2006.01)
*A61B 17/072* (2006.01)
*H01M 2/10* (2006.01)
*H01M 10/44* (2006.01)
(Continued)

(52) U.S. Cl.
CPC ...... *A61B 17/072* (2013.01); *A61B 17/07207* (2013.01); *H01M 2/1022* (2013.01); *H01M 10/4257* (2013.01); *H01M 10/44* (2013.01); *H02J 7/0068* (2013.01); *A61B 2017/00017* (2013.01); *A61B 2017/00039* (2013.01); *A61B 2017/0046* (2013.01); *A61B 2017/00398* (2013.01); *A61B 2017/00473* (2013.01); *A61B 2017/00734* (2013.01); *A61B 2017/07285* (2013.01); *A61B 2560/0204* (2013.01); *H01M 2220/30* (2013.01); *H02J 7/0036* (2013.01); *H02J 7/0045* (2013.01); *H02J 2007/0067* (2013.01)

(58) Field of Classification Search
CPC .......... H01M 2/1022; H01M 10/4257; H01M 10/44; A61B 17/072
USPC ......................................................... 173/1
See application file for complete search history.

(56) References Cited

U.S. PATENT DOCUMENTS

| 4,805,823 A | 2/1989 | Rothfuss |
| 5,415,334 A | 5/1995 | Williamson, IV et al. |
| 5,465,895 A | 11/1995 | Knodel et al. |
(Continued)

OTHER PUBLICATIONS

Extended European Search Report dated Feb. 8, 2017 for Application No. 16191192.0, 9 pages.
(Continued)

*Primary Examiner* — Gloria R Weeks
(74) *Attorney, Agent, or Firm* — Frost Brown Todd LLC

(57) ABSTRACT

A surgical instrument includes a shaft assembly, a handle assembly including a battery dock, and a battery unit. The battery unit is configured to be received by the battery dock such that the battery unit is in electrical communication with at least one of the shaft assembly or the handle assembly. The battery unit includes a casing, an anode contact and a cathode contact within the casing, and a discharge drain. The discharge drain includes a controller, a switch element, and a resistor element operatively connected between the cathode contact and the anode contact. The controller is configured to selectively direct the switch element to close such that the resistor element is in electrical communication with the anode contact and the cathode contact. Thereby, the resistor element is configured to drain a remaining electrical power from the at least one battery connected to the anode contact and the cathode contact.

20 Claims, 25 Drawing Sheets

(51) Int. Cl.
*A61B 17/00* (2006.01)
*H02J 7/00* (2006.01)

(56) References Cited

U.S. PATENT DOCUMENTS

| | | | |
|---|---|---|---|
| 5,597,107 A | 1/1997 | Knodel et al. | |
| 5,632,432 A | 5/1997 | Schultze et al. | |
| 5,673,840 A | 10/1997 | Schultze et al. | |
| 5,704,534 A | 1/1998 | Huitema et al. | |
| 5,814,055 A | 9/1998 | Knodel et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,007,762 B2 * | 3/2006 | Yamamoto | B25B 21/00 173/1 |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,632,525 B2 | 1/2014 | Kerr et al. | |
| 8,695,866 B2 | 4/2014 | Leimbach et al. | |
| 9,072,535 B2 | 7/2015 | Shelton, IV et al. | |
| 9,112,248 B2 * | 8/2015 | Johnson | B25F 5/00 |
| 9,186,142 B2 | 11/2015 | Fanelli et al. | |
| 9,289,212 B2 | 3/2016 | Shelton, IV et al. | |
| 9,517,065 B2 | 12/2016 | Simms et al. | |
| 2011/0017801 A1 * | 1/2011 | Zemlok | A61B 17/07207 227/175.1 |
| 2012/0071866 A1 * | 3/2012 | Kerr | A61B 17/07207 606/13 |
| 2012/0080477 A1 * | 4/2012 | Leimbach | A61B 17/07207 227/175.2 |
| 2013/0103023 A1 * | 4/2013 | Monson | H02J 7/00 606/33 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0263541 A1 | 9/2014 | Leimbach et al. | |
| 2015/0272575 A1 | 10/2015 | Leimbach et al. | |
| 2016/0106425 A1 * | 4/2016 | Yates | A61B 17/07207 320/113 |
| 2016/0374673 A1 * | 12/2016 | Stager | A61B 17/0644 227/176.1 |

OTHER PUBLICATIONS

European Examination Report dated Sep. 7, 2018 for Application No. EP 16191192.0, 6 pgs.
International Search Report and Written Opinion dated Dec. 16, 2016 for Application No. PCT/US2016/052770, 12 pgs.

* cited by examiner

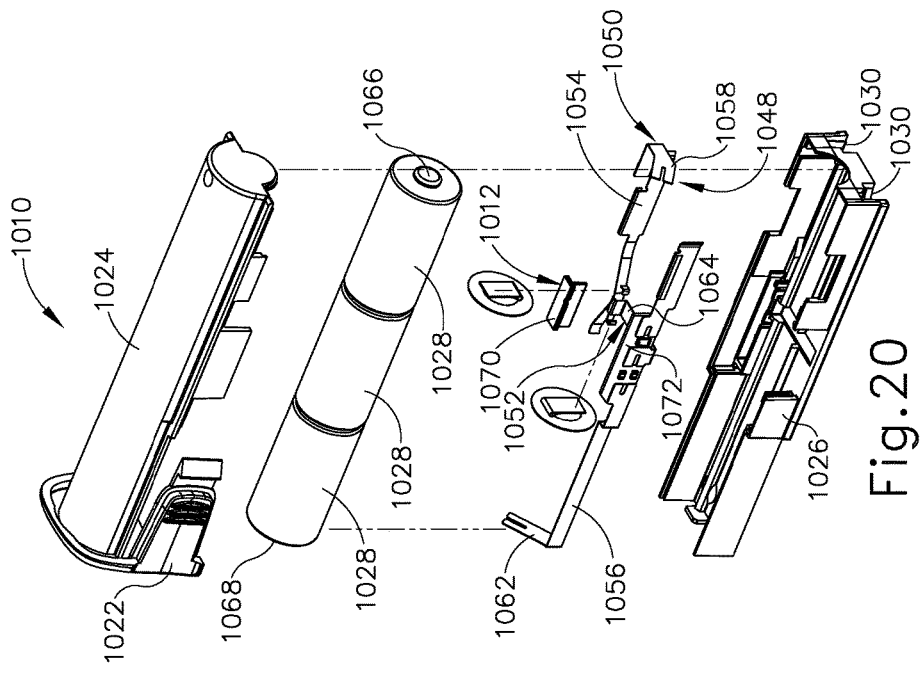
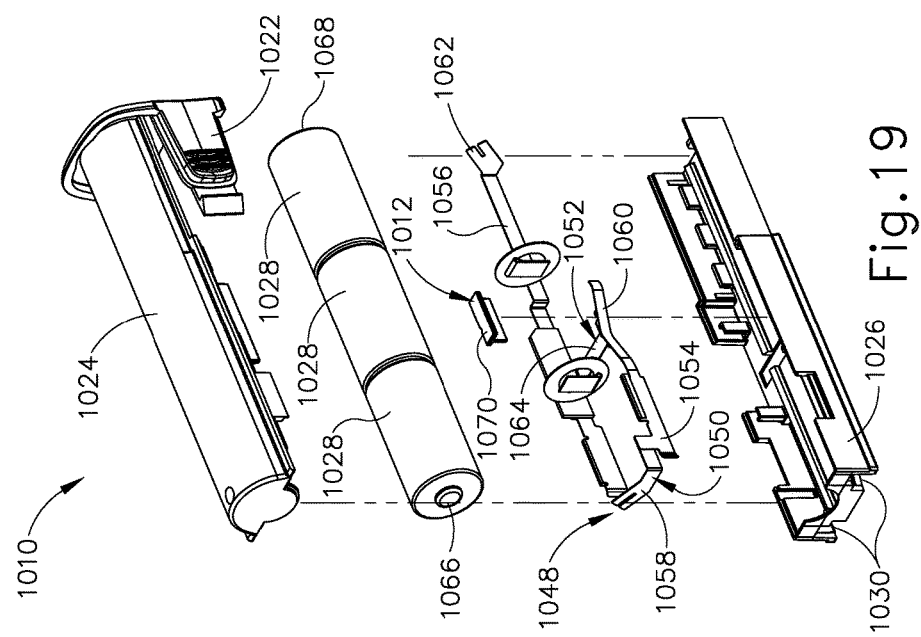

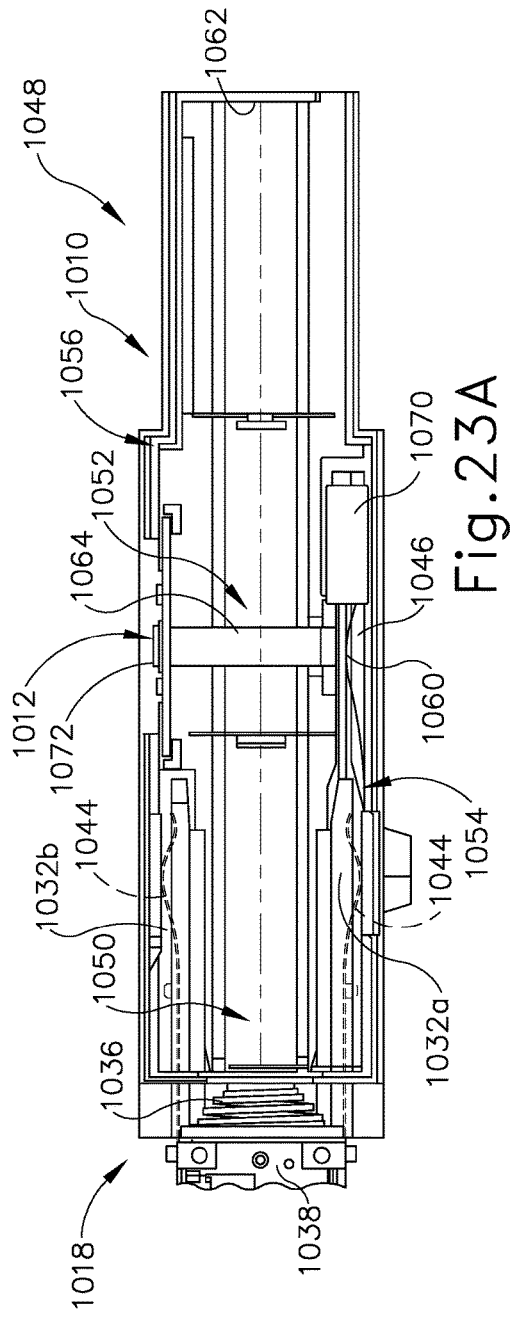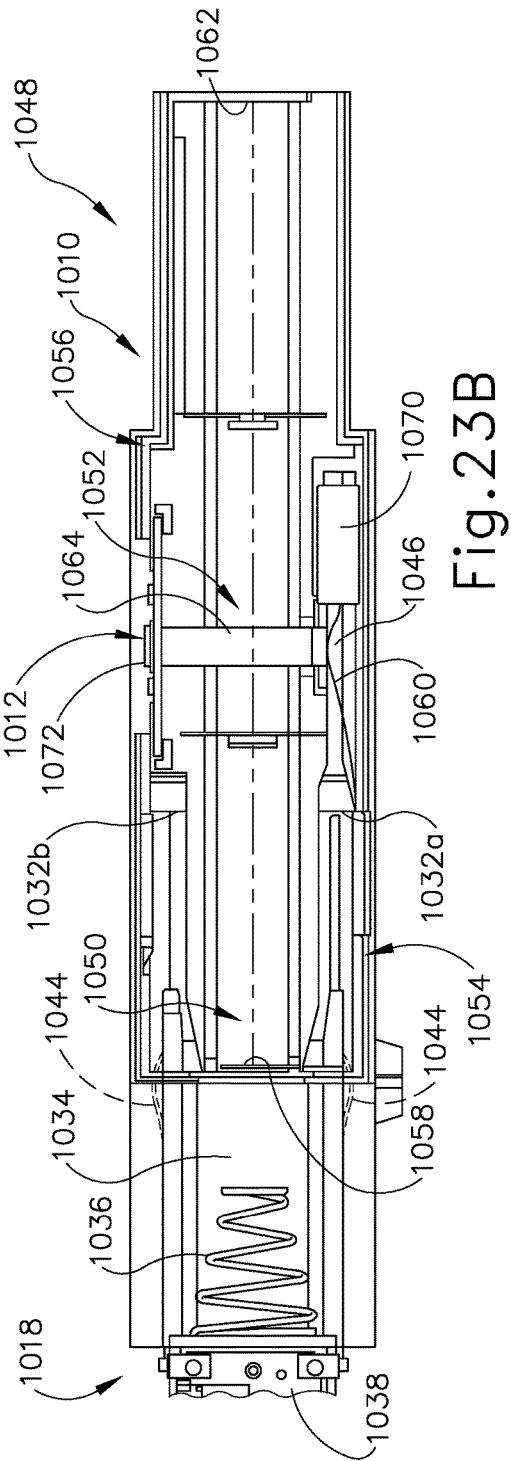

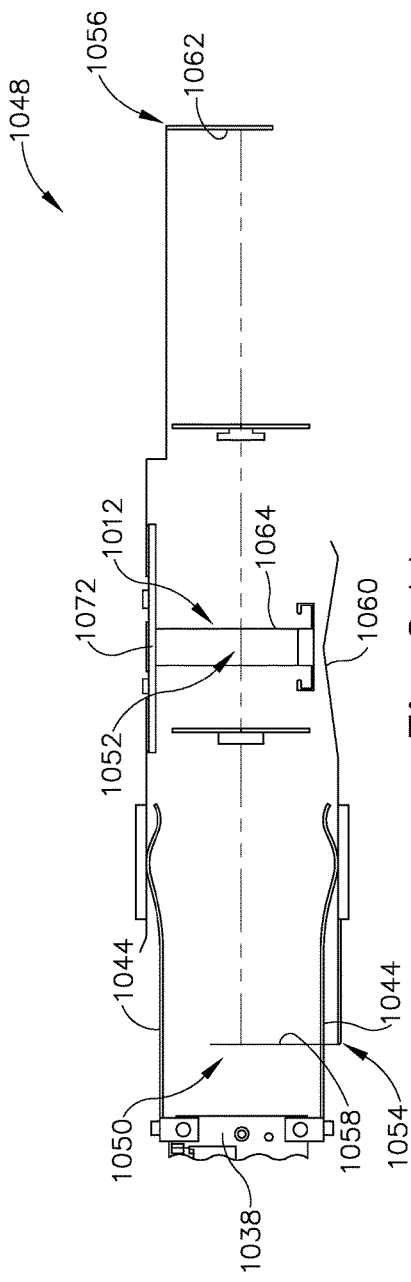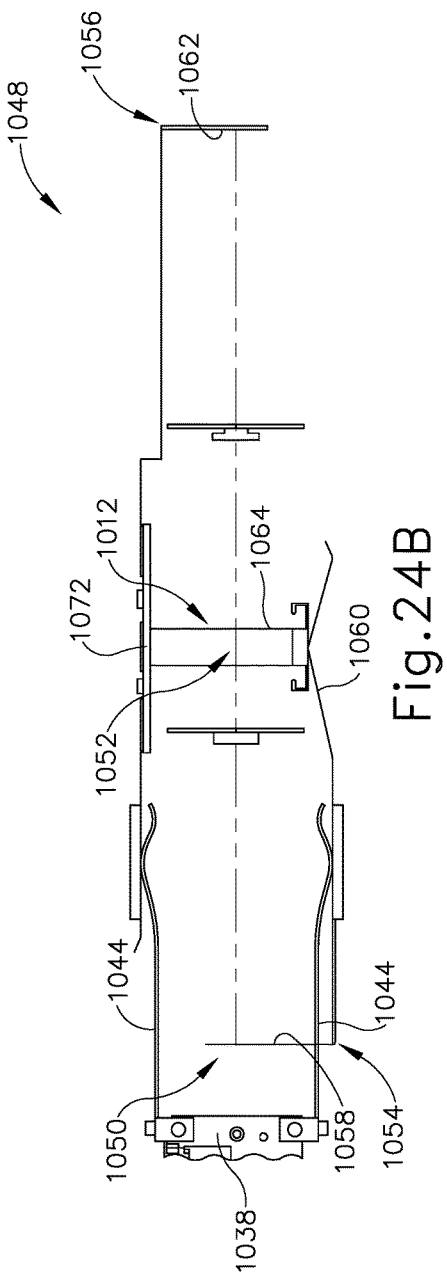

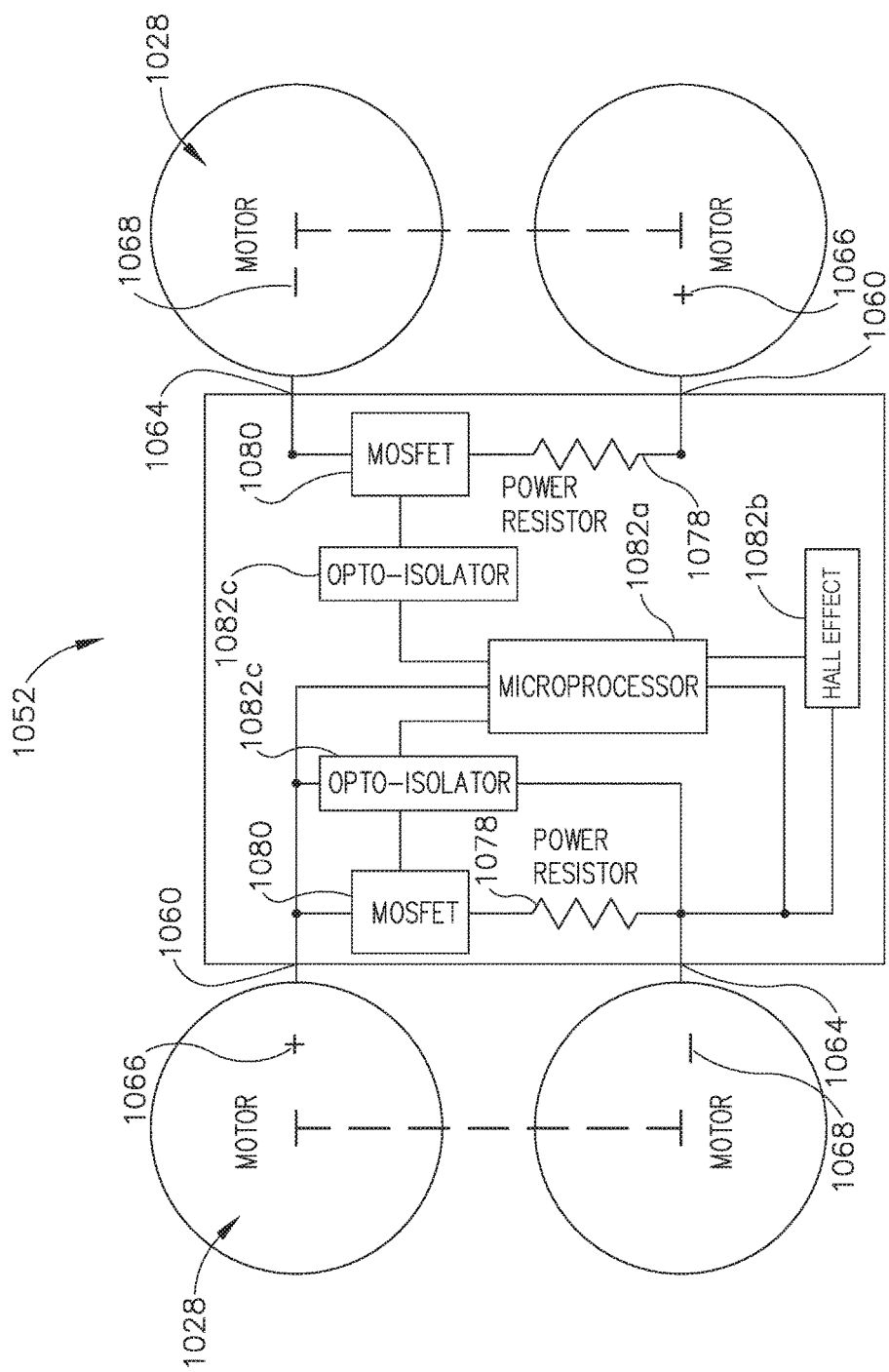

BATTERY DRAIN CIRCUIT FOR SURGICAL INSTRUMENT

BACKGROUND

Various kinds of surgical instruments may be powered by one or more battery cells. Such instruments may be used in a variety of surgical environments including, for example, endoscopic environments, laparoscopic environments, and open environments. Battery-powered surgical instruments may include motor-driven implements, such as cutters, graspers, and/or staplers, for example. Battery-powered surgical instruments may also include non-motor driven implements, such as RF cutter/coagulators, ultrasonic cutter/coagulators, and/or laser cutter/coagulators, for example.

Battery-powered surgical instruments may utilize primary cells, which are pre-charged and intended for a single discharge (e.g., one use). Using single discharge cells avoids the difficulties that may be associated with re-sterilizing and recharging cells. Primary cells, however, may present challenges related to shipping, storage, and disposal. For example, some charged cells can result in hazardous waste if not properly discharged since they may be only used once and may still have significant amount of charge left. To mitigate the risks, some jurisdictions have regulations governing the conditions under which cells may be shipped and disposed. Cells and batteries with higher amounts of stored energy may be required to be shipped, stored, and disposed of with safety measures that are more stringent and often more expensive.

Examples of battery-powered surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, issued as U.S. Pat. No. 9,186,142 on Nov. 17, 2015; U.S. Patent Application Publication No. 2014/0239041, entitled "Lockout Feature for Movable Cutting Member of Surgical Instrument," Published Aug. 28, 2014 issued as U.S. Pat. No. 9,717,479 on Aug. 1, 2017; U.S. Patent Application Publication No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Application Publication No. 2014/0239036, entitled "Jaw Closure Feature for End Effector of Surgical Instrument," Published Aug. 28, 2014, issued as U.S. Pat. No. 9,839,421 on Dec. 12, 2017; U.S. Patent Application Publication No. 2014/0239040, entitled "Surgical Instrument with Articulation Lock having a Detenting Binary Spring," published Aug. 24, 2014, issued as U.S. Pat. No. 9,867,615 on Jan. 16, 2018; U.S. Patent Application Publication No. 2014/0239043, entitled "Distal Tip Features for End Effector of Surgical Instrument," published Aug. 28, 2014, issued as U.S. Pat. No. 9,622,746 on Apr. 18, 2017; U.S. Patent Application Publication No. 2014/0239037, entitled "Staple Forming Features for Surgical Stapling Instrument," filed Aug. 28, 2014, issued as U.S. Pat. No. 10,092,292 on Oct. 9, 2018; U.S. Patent Application Publication No. 2014/0239038, entitled "Surgical Instrument with Multi-Diameter Shaft," published Aug. 28, 2014, issued as U.S. Pat. No. 9,795,379 on Oct. 24, 2017; and U.S. Patent Application Publication No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Applications is incorporated by reference herein While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 19 depicts an exploded left perspective view of the power source of FIG. 16;

FIG. 20 depicts an exploded right perspective view of the power source of FIG. 16;

FIG. 23A depicts an enlarged cross-sectional plan view of the instrument of FIG. 15 taken generally along a centerline of the power source, with an exemplary power drain in an open position;

FIG. 23B depicts an enlarged cross-sectional plan view of the instrument of FIG. 15 taken generally along a centerline of the power source, with the power drain of FIG. 23A in a closed position;

FIG. 24A depicts an enlarged cross-sectional plan view of the instrument of FIG. 15 taken generally along a centerline of the power source, with certain components omitted for clarity, and with the power drain of FIG. 23A in the open position;

FIG. 24B depicts an enlarged cross-sectional plan view of the instrument of FIG. 15 taken generally along a centerline of the power source, with certain components omitted for clarity, and with the power drain of FIG. 23A in the closed position;

FIG. 25 depicts a schematic circuit diagram of an exemplary power drain circuit;

Figure 1:
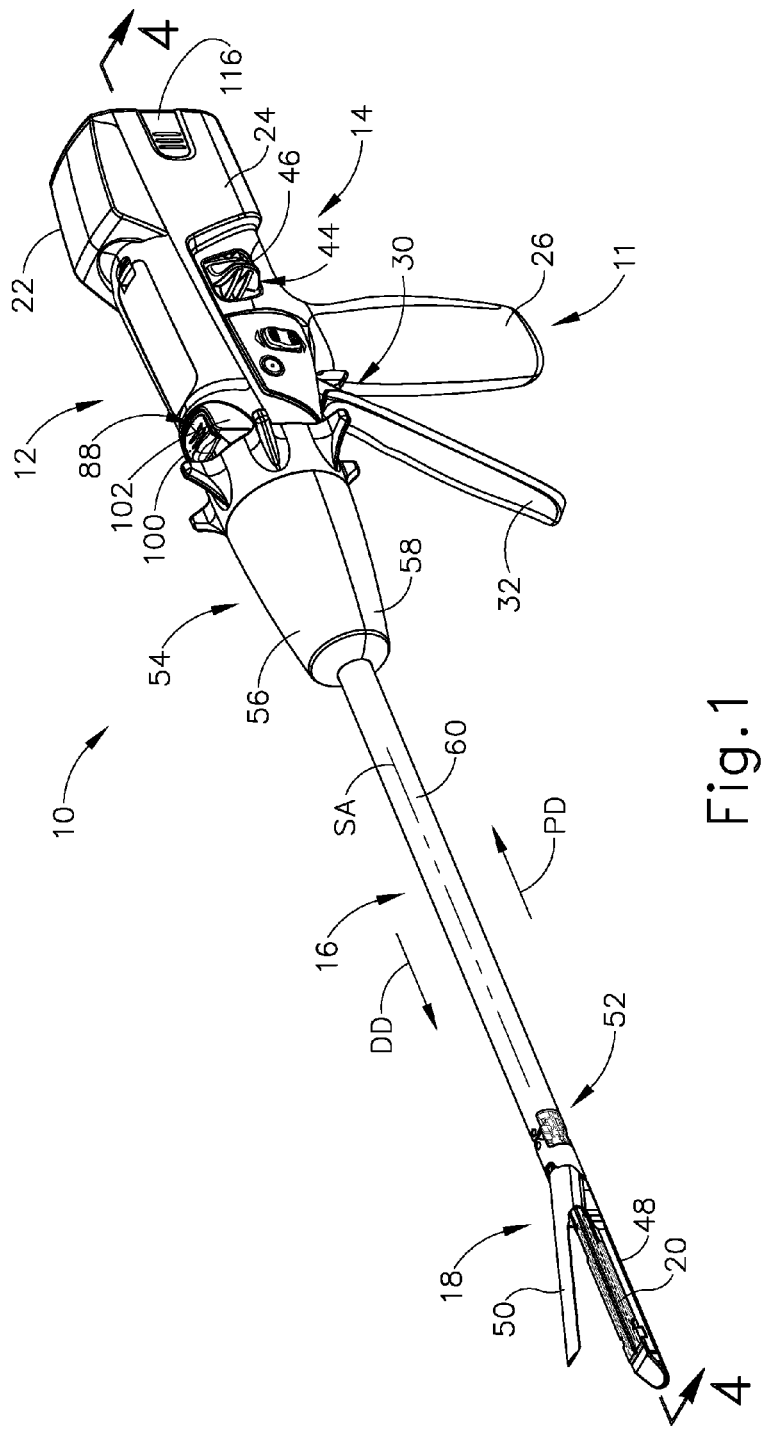
FIG. 1 depicts a perspective view of an exemplary surgical stapling instrument including an interchangeable shaft assembly, a handle assembly, and a removable battery assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator. Similarly, the terms "left" and "right" are define herein relative to the operator or other operators grasping the surgical instrument. Although the surgical instruments described herein comprise motorized implements for cutting and stapling, it will be appreciated that the battery configurations described herein may be used with any suitable type of electrical surgical instrument such as cutters, claspers, staplers, RF cutter/coagulators, ultrasonic cutter/coagulators, and laser cutter/coagulators, for example.

I. Overview of Exemplary Surgical Instrument

FIG. 1 depicts a motor-driven surgical cutting and fastening instrument (10) that may or may not be reused. In the illustrated embodiment, surgical instrument (10) includes a handle assembly (11) having a housing (12). At least a portion of the housing (12) forms a handle (14) configured to be grasped, manipulated and actuated by the clinician. Housing (12) is configured for operative attachment to an interchangeable shaft assembly (16) that has a surgical end effector (18) operatively coupled thereto that is configured to perform one or more surgical tasks or procedures. It will be appreciated that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operatively supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operatively control a surgical instrument. For example, the interchangeable shaft assemblies disclosed herein may be employed with various robotic systems, instruments, components and methods disclosed in U.S. Pat. No. 9,072,535, entitled "Surgical Stapling Instruments with Rotatable Staple Deployment Arrangements," issued Jul. 7, 2015, the disclosure of which is incorporated by reference herein.

Handle assembly (11) is shown in connection with the interchangeable shaft assembly (16) that includes end effector (18), which is operable to sever tissue and apply staples to tissue as described in various references cited herein. Housing (12) may be configured for use in connection with interchangeable shaft assemblies that include end effectors that are adapted to support different sizes and types of staple cartridges, have different shaft lengths, sizes, and types, etc. In addition, handle assembly (11) may also be effectively employed with a variety of other interchangeable shaft assemblies including those assemblies that are configured to apply other motions and fauns of energy such as, for example, radio frequency (RF) energy, ultrasonic energy and/or motion to end effector arrangements adapted for use in connection with various surgical applications and procedures. Furthermore, end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly. Various examples of such cartridges are disclosed in various references that are cited herein.

Figure 2:
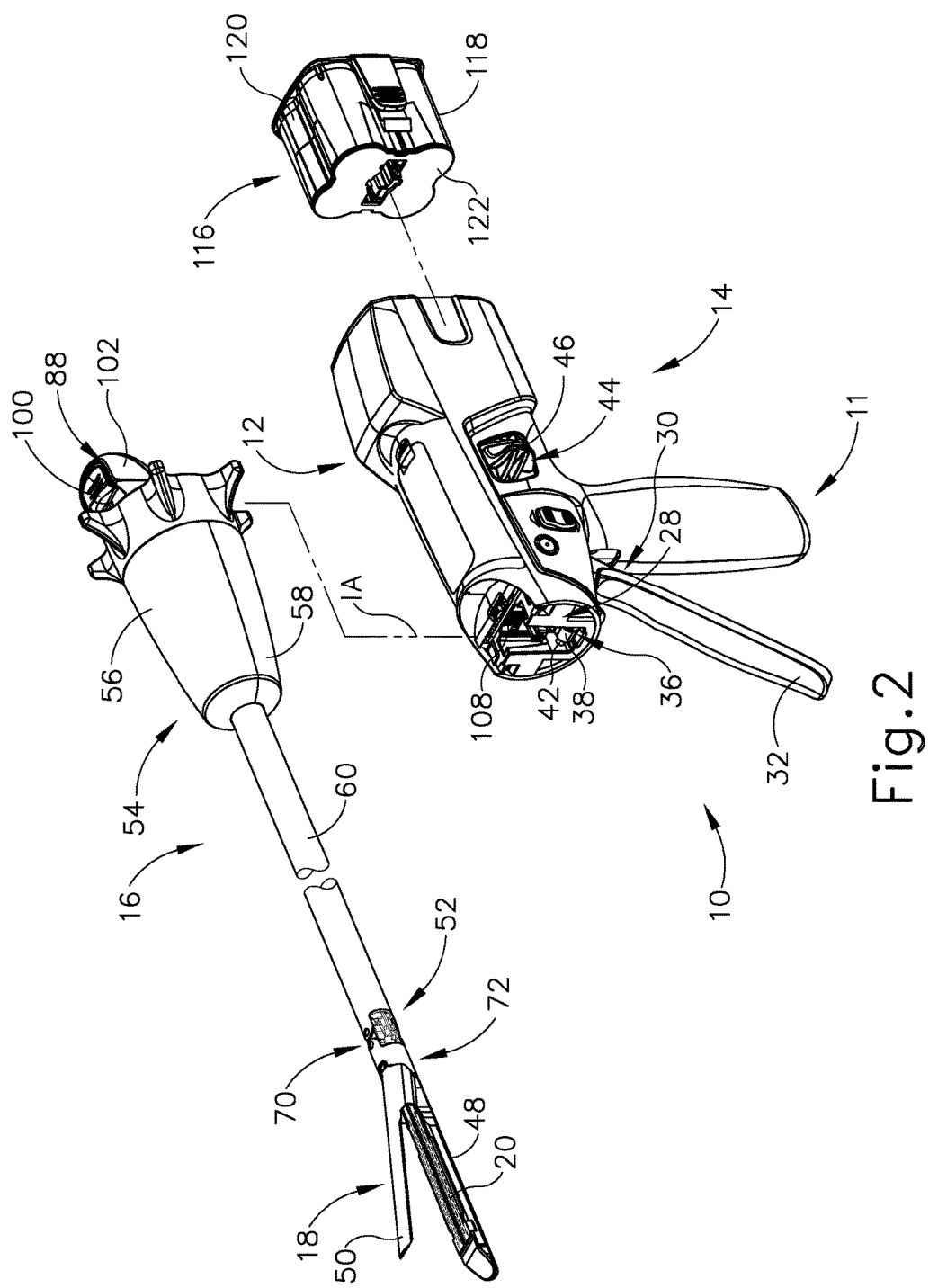
FIG. 2 depicts an perspective view of the instrument of FIG. 1, showing the shaft assembly and battery assembly disassembled from the handle assembly of the instrument.
Figure 3:
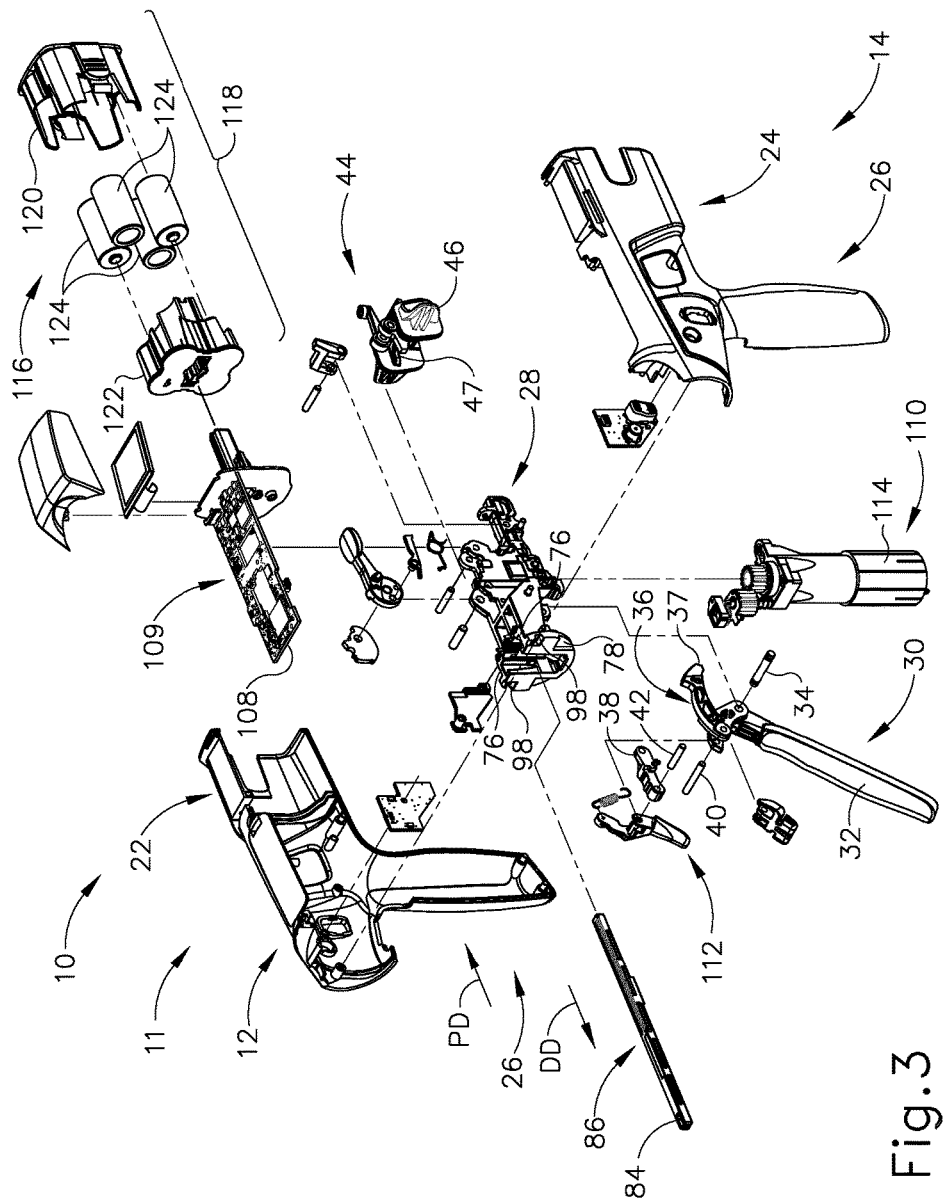
FIG. 3 depicts an exploded view of the handle assembly and battery assembly of the instrument of FIG. 1.

FIG. 1 illustrates surgical instrument (10) with interchangeable shaft assembly (16) operatively coupled to handle assembly (11). FIGS. 2-3 illustrate attachment of interchangeable shaft assembly (16) to housing (12) of handle (14). Handle (14) includes a pair of interconnectable handle housing segments (22, 24) that may be interconnected by screws, snap features, adhesive, etc. In the illustrated arrangement, handle housing segments (22, 24) cooperate to form a pistol grip portion (26) that can be gripped and manipulated by the clinician. As will be discussed in further detail below, handle (14) operatively supports a plurality of drive systems therein that are configured to generate and apply various control motions to corresponding portions of interchangeable shaft assembly (16) that is operatively attached thereto.

Handle (14) further includes a frame (28) that operatively supports a plurality of drive systems. For example, frame (28) can operatively support a "first" or closure drive system, generally designated as (30), which may be employed to apply closing and opening motions to interchangeable shaft assembly (16) that is operatively attached or coupled thereto. In one example, closure drive system (30) includes an actuator in the form of a closure trigger (32) that is pivotally supported by frame (28). More specifically, closure trigger (32) is pivotally coupled to housing (14) by a pin (34) (see FIG. 4A). Such arrangement enables closure trigger (32) to be manipulated by a clinician such that when the clinician grips pistol grip portion (26) of handle (14), closure trigger (32) may be easily pivoted from a starting or "unactuated" position toward pistol grip portion (26) to an "actuated" position and more particularly to a fully compressed or fully actuated position. Closure trigger (32) may be biased into the unactuated position by spring or other biasing arrangement (not shown). In various examples, closure drive system (30) further includes a closure linkage assembly (36) pivotally coupled to closure trigger (32). The closure linkage assembly (36) may include a first closure link (not shown) and a second closure link (38) that are pivotally coupled to closure trigger (32) by a pin (not shown). Second closure link (38) may also be referred to herein as an "attachment member" and include a transverse attachment pin (37).

Still referring to FIGS. 1-3, first closure link (not shown) is configured to cooperate with a closure release assembly (44) that is pivotally coupled to frame (28). In at least one example, closure release assembly (44) has a release button assembly (46) with a distally protruding locking pawl (not shown) formed thereon. Release button assembly (46) may be pivoted in a counterclockwise direction by a release spring (not shown). As the clinician depresses closure trigger (32) from its unactuated position toward pistol grip portion (26) of handle (14), first closure link (not shown) pivots upward to a point where a locking pawl (not shown) drops into retaining engagement with first closure link (not shown) thereby preventing closure trigger (32) from returning to the unactuated position. Thus, closure release assembly (44) serves to lock closure trigger (32) in the fully actuated position. When the clinician desires to unlock closure trigger (32) from the actuated position to return to the unactuated position, the clinician simply pivots closure release button assembly (46) such that locking pawl (not shown) is moved out of engagement with the first closure link (not shown). When the locking pawl (not shown) has been moved out of engagement with first closure link (not shown), closure trigger (32) may pivot back to the unactuated position. Other closure trigger locking and release arrangements may also be employed.

Interchangeable shaft assembly (16) includes surgical end effector (18) that comprises an elongated lower jaw (48) that is configured to operatively support staple cartridge (20) therein. End effector (18) of the present example further includes an anvil (50) that is pivotally supported relative to elongated channel (48). Interchangeable shaft assembly (16) further includes an articulation joint (52) and an articulation lock (not shown) that can be configured to releasably hold end effector (18) in a desired position relative to a longitudinal axis of shaft assembly (16). By way of example only, end effector (18), articulation joint (52), and articulation lock (not shown) may be configured and operable in accordance with at least some of the teachings of U.S. Pub. No. 2014/0263541, entitled "Articulatable Surgical Instrument Comprising an Articulation Lock," published Sep. 18, 2014, now abandoned. Alternatively, end effector (18), articulation joint (52), and articulation lock (not shown) may be configured and operable in accordance with at least some of the teachings of any other reference(s) cited herein; or may be configured and operable in any other suitable fashion.

Interchangeable shaft assembly (16) further includes a proximal housing or nozzle (54) comprised of nozzle portions (56, 58). Interchangeable shaft assembly (16) further includes a closure tube (60) which can be utilized to close and/or open anvil (50) of end effector (18). Shaft assembly (16) also includes a closure shuttle (62) that is slidably supported within a chassis (64) such that it may be axially moved relative thereto. Closure shuttle (62) includes a pair of proximally-protruding hooks (66) that are configured for attachment to attachment pin (42) that is attached to second closure link (38). A proximal end (68) (see FIG. 5A) of closure tube (60) is coupled to closure shuttle (62) for relative rotation thereto. A closure spring (not shown) is journaled on closure tube (60) and serves to bias closure tube (60) in the proximal direction (PD), which can serve to pivot closure trigger (32) into the unactuated position when shaft assembly (16) is operatively coupled to handle (14). Additional details regarding one or more features of alternative shaft assemblies will be provided below in greater detail.

Interchangeable shaft assembly (16) further includes articulation joint (52).

Other interchangeable shaft assemblies, however, may not be capable of articulation. By way of example, articulation joint (52) includes a double pivot closure sleeve assembly (70). The double pivot closure sleeve assembly (70) includes an end effector closure sleeve assembly (72) for engaging an opening tab on anvil (50) in the various manners described in U.S. Pub. No. 2014/0263541, the disclosure of which is incorporated by reference herein, now abandoned. While shaft assembly (16) of the present example includes articulation joint (52), other interchangeable shaft assemblies may lack articulation capabilities.

Figure 4:
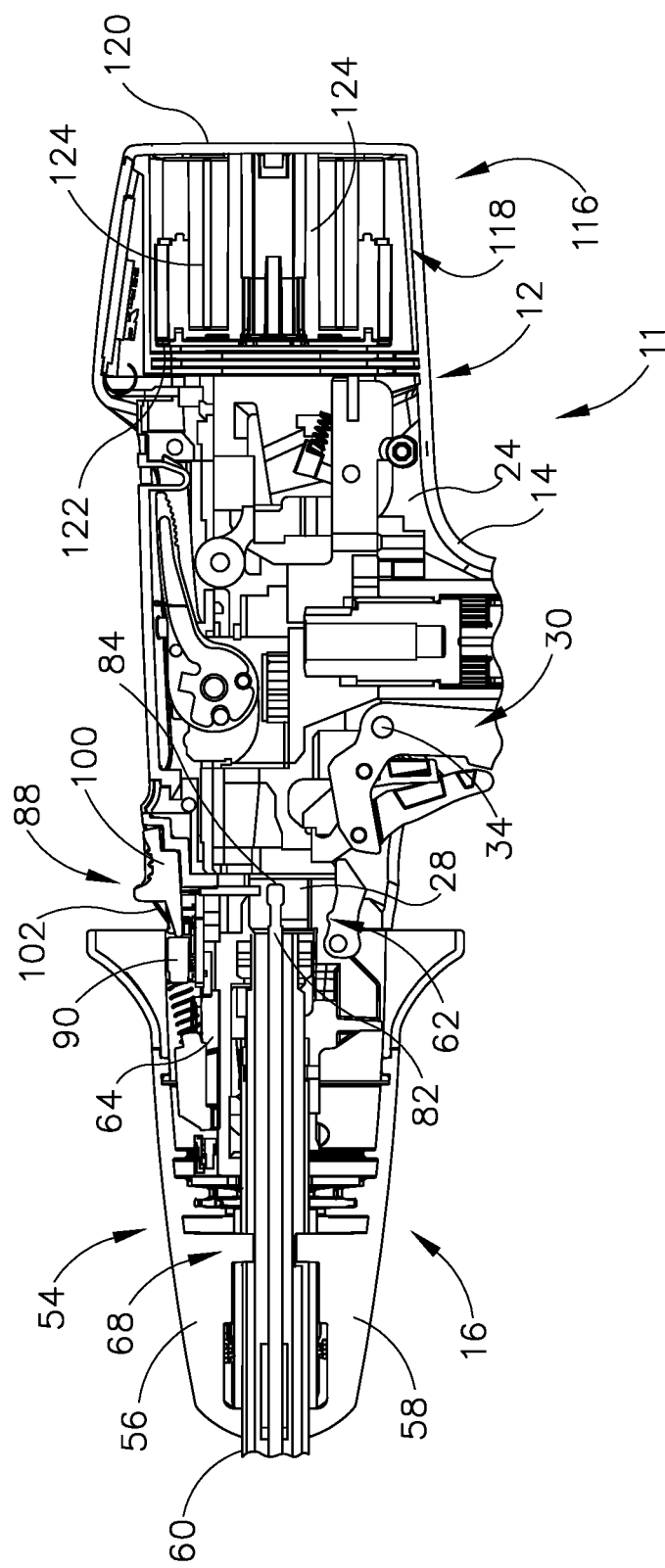
FIG. 4 depicts a cross-sectional side view of the instrument of FIG. 1, taken along line 4-4 of FIG. 1, with the shaft assembly operatively coupled to the handle assembly.

Referring to FIGS. 2-4, chassis (64) includes at least one, and preferably two, tapered attachment portions (not shown) formed thereon that are adapted to be received within corresponding dovetail slots (76) formed within a distal attachment flange portion (78) of frame (28). Each dovetail slot (76) may be tapered or, stated another way, be somewhat V-shaped to seatingly receive attachment portions (not shown) therein. A shaft attachment lug (not shown) is formed on the proximal end of an intermediate firing shaft (82). As such, when interchangeable shaft assembly (16) is coupled to handle (14), shaft attachment lug (not shown) is received in a firing shaft attachment cradle (84) formed in a distal end of a longitudinal drive member (86).

One example of shaft assembly (16) includes a latch system (88) for removably coupling shaft assembly (16) to handle assembly (11) and, more specifically, to frame (28). For example, latch system (88) includes a lock member or lock yoke (90) that is movably coupled to chassis (64). In the illustrated embodiment, for example, lock yoke (90) has a U-shape with two spaced downwardly extending legs (not shown). Legs (not shown) each have a pivot lug (not shown) formed thereon that are adapted to be received in corresponding holes (not shown) formed in chassis (64). Such arrangement facilitates pivotal attachment of lock yoke (90) to chassis (64). Lock yoke (90) includes two proximally protruding lock lugs (not shown) that are configured for releasable engagement with corresponding lock detents or grooves (98) in distal attachment flange portion (78) of frame (28). In various forms, lock yoke (90) is biased in the proximal direction by spring or biasing member (not shown). Actuation of lock yoke (90) may be accomplished by a latch button (100) that is slidably mounted on a latch actuator assembly (102) that is mounted to chassis (64). Latch button (100) may be biased in a proximal direction relative to lock yoke (90). As will be discussed in further detail below, lock yoke (90) may be moved to an unlocked position by biasing latch button (100) the in distal direction, which also causes lock yoke (90) to pivot out of retaining engagement with distal attachment flange portion (78) of frame (28). When lock yoke (90) is in "retaining engagement" with distal attachment flange portion (78) of frame (28), lock lugs (not shown) are retainingly seated within the corresponding lock detents or grooves (98) in distal attachment flange portion (78).

When employing an interchangeable shaft assembly that includes an end effector of the type described herein that is adapted to cut and fasten tissue, as well as other types of end effectors, it may be desirable to prevent inadvertent detachment of the interchangeable shaft assembly (16) from the handle assembly (11) during actuation of end effector (18). For example, in use, the clinician may actuate the closure trigger (32) to grasp and manipulate the target tissue into a desired position. Once the target tissue is positioned within end effector (18) in a desired orientation, the clinician may then fully actuate closure trigger (32) to close anvil (50) and clamp the target tissue in position for cutting and stapling. In that instance, closure drive system (30) has been fully actuated. After the target tissue has been clamped in the end effector (18), it may be desirable to prevent the inadvertent detachment of shaft assembly (16) from handle assembly (11).

To this end, lock yoke (90) includes at least one and preferably two lock hooks (not shown) that are adapted to contact corresponding lock lugs (not shown) that are formed on closure shuttle (62). When closure shuttle (62) is in an unactuated position (i.e., the first drive system (30) is unactuated and anvil (50) is open), lock yoke (90) may be pivoted in a distal direction to unlock interchangeable shaft assembly (16) from handle assembly (11). When in that position, lock hooks (not shown) do not contact the lock lugs (not shown) on closure shuttle (62). However, when closure shuttle (62) is moved to an actuated position (i.e., the first drive system (30) is actuated and the anvil (50) is in the closed position), lock yoke (90) is prevented from being pivoted to an unlocked position. Stated another way, if the clinician were to attempt to pivot lock yoke (90) to an unlocked position or, for example, lock yoke (90) was inadvertently bumped or contacted in a manner that might otherwise cause it to pivot distally, lock hooks (not shown) on lock yoke (90) will contact lock lugs (not shown) on closure shuttle (62) and prevent movement of lock yoke (90) to an unlocked position.

An electrical connector (108) on handle control board (109) communicates with a firing drive system (110) for operating surgical instrument (10). Firing drive system (110) operatively connects a firing trigger (112) of handle (14) with the intermediate firing shaft (82) of shaft assembly (16). Firing drive system (110) of the present example employs an electric motor (114), located in pistol grip portion (26) of handle assembly (11). In various examples, motor (114) may be a DC brushed driving motor having a maximum rotation of, approximately, 25,000 RPM, for example. In other arrangements, motor (114) may include a brushless motor, a cordless motor, a synchronous motor, a stepper motor, or any other suitable electric motor. Motor (114) is powered by a power source (116) that in one the present example comprises a removable battery unit (118). As can be seen in FIGS. 3-4, battery unit (118) of the present example comprises a proximal housing portion (120) that is configured for attachment to a distal housing portion (122). Proximal housing portion (120) and distal housing portion (122) are configured to operatively support a plurality of batteries (124) therein. Batteries (124) may each comprise, for example, a Lithium Ion ("LI") battery or other suitable battery. Distal housing portion (122) is configured for removable operable attachment to control circuit board assembly (109), which is also operatively coupled to motor (114). A number of batteries (124) may be connected in series to be used as power source (116) for surgical instrument (10). In addition, power source (116) may be replaceable and/or rechargeable.

As discussed above, at least five systems of the interchangeable shaft assembly (16) may be operatively coupled with at least five corresponding systems of the handle (14). A first system comprises a frame system that couples and/or aligns the frame or spine of shaft assembly (16) with frame (28) of the handle (14). A second system is closure drive system (30) that may operatively connect closure trigger (32) of handle (14) and closure tube (60) and anvil (50) of shaft assembly (16). As outlined above, closure shuttle (62) of shaft assembly (16) engages with pin (42) on second closure link (38). A third system is a firing drive system operatively connecting a firing trigger the handle (14) with the intermediate firing shaft (82) of the shaft assembly (16). As outlined above, the shaft attachment lug (80) operatively connects with the cradle (84) of the longitudinal drive member (86). A fourth system is an electrical system that can signal to a controller in the handle (14), such as microcontroller, that the shaft assembly (16) has been operatively engaged with the handle (14) to conduct power and/or communicate signals between the shaft assembly (16) and the handle (14). For instance, the shaft assembly (16) includes an electrical connector (106) that is operatively mounted to a shaft circuit board (not shown). Electrical connector (106) is configured for mating engagement with a corresponding electrical connector (108) on a handle control board (not shown). Further details regarding the circuitry and control systems may be found in U.S. Pub. No. 2014/0263541, the disclosure of which is incorporated by reference herein. The fifth system is latch system (88) for releasably locking the shaft assembly (16) to the handle (14).

The various shaft assemblies (16) disclosed herein may employ sensors and various other components that require electrical communication with the controller in the housing (12). These shaft assemblies (16) generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion. In addition to the foregoing, instrument (10) may be constructed and operable in accordance with at least some of the teachings of U.S. patent application Ser. No. 14/226,142, entitled "Surgical Instrument Comprising a Sensor System," filed Mar. 26, 2014, issued as U.S. Pat. No. 9,913,643 on Mar. 13, 2018, the disclosure of which is incorporated by reference herein. In addition or in the alternative, instrument (10) may be constructed and operable in accordance with at least some of the teachings of any of the various other references that are cited herein.

II. Exemplary Power Sources and Various Battery Units

Figure 5:
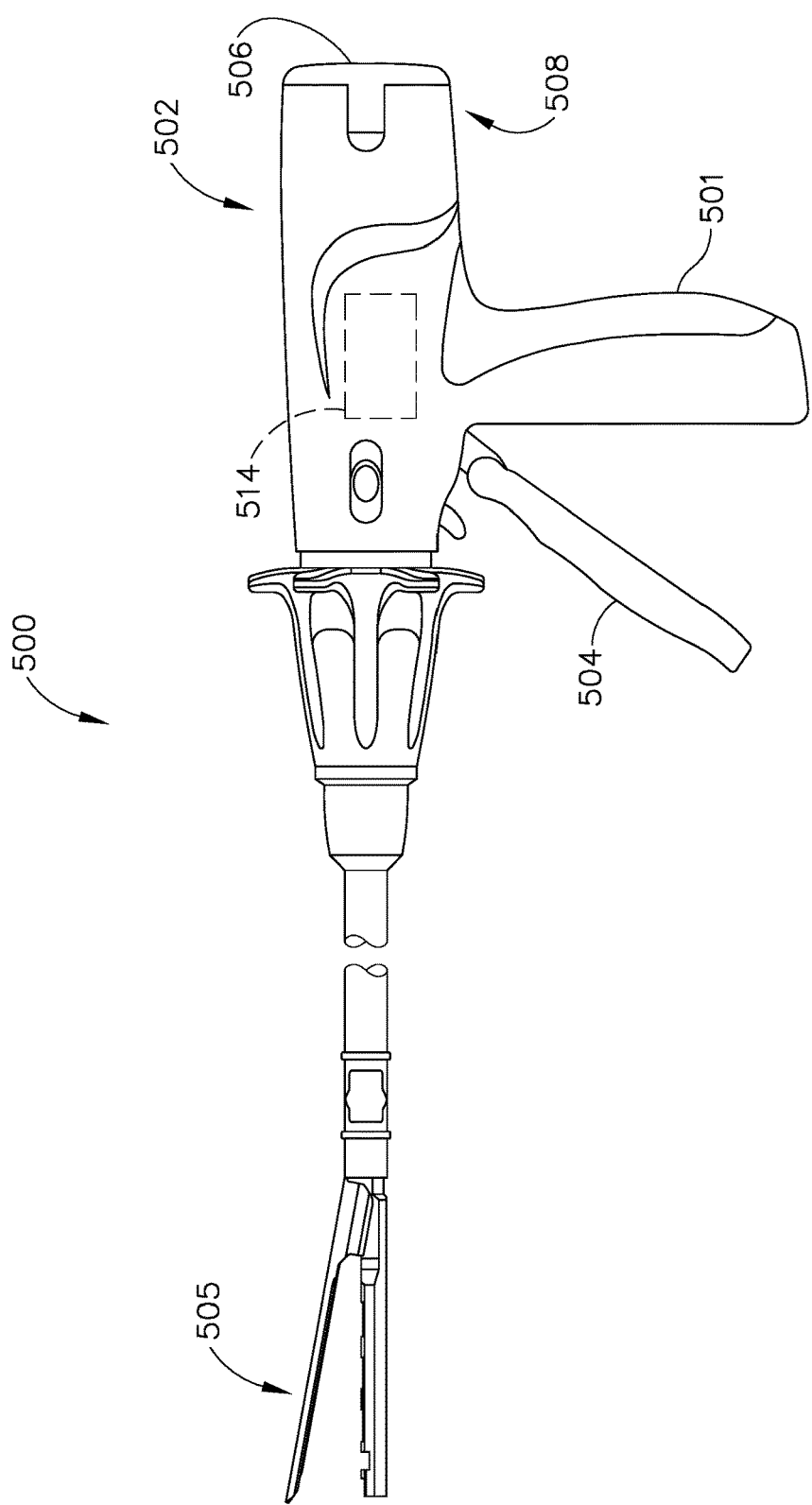
FIG. 5 depicts a side view of another exemplary surgical stapling instrument having a handle assembly and a power source.

FIG. 5 illustrates another exemplary instrument (500), which is substantially identical to instrument (10), except for the differences as described below. Surgical instrument (500) comprises a pistol grip (501), a handle (502), a trigger (504) and an end effector (505). Handle (502), trigger (504) and end effector (505) may operate in a manner similar to that described with respect to shaft assembly (16) having end effector (18) and handle assembly (11) described above.

Handle (502) of surgical instrument (500) houses at least one battery unit (506). Battery unit (506) may comprise a single battery or a plurality of batteries arranged in a series and/or parallel configuration. Handle (502) includes a battery dock (508) to which battery unit (506) may be attached. Battery dock (508) may comprise any suitable structure for coupling battery unit (506) to surgical instrument (500). For example, battery dock (508) may comprise a cavity in handle (502) that is configured to receive at least a portion of battery unit (506), as illustrated. In other versions, battery dock (508) may be implemented using a variety of other structures. For instance, some versions of battery dock (508) may comprise a post that is received by battery unit (506). In addition or in the alternative, pistol grip (501) may comprise battery dock (508).

As discussed in more detail below, battery dock (508) of the present example comprises a protruding portion that is configured to interact with battery unit (506) upon attachment of battery unit (506) to handle (502). Once attached, battery unit (506) will be electrically connected to and provide power to a circuit (514) of surgical instrument (500). Circuit (514) may be located in handle (502) as shown, in end effector (505), or in any combination of locations within surgical instrument (500). In use, circuit (514) may power the operation of at least one surgical implement at end effector (505). For example, circuit (514) may comprise an electric motor for operating an electrically powered cutter, stapler, clasper, or other mechanical device. In addition to, or instead of a motor, circuit (514) may comprise suitable circuit components for implementing an RF, ultrasonic, or other type of non-motor-powered surgical implement.

Figure 6A:
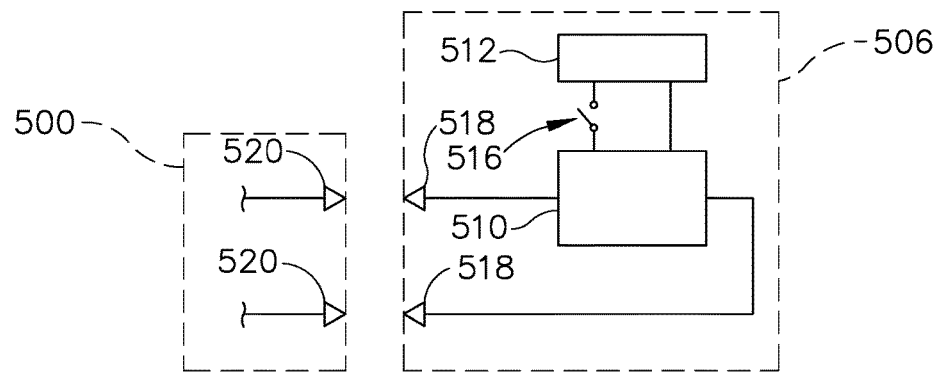
FIG. 6A depicts a schematic diagram of the power source detached from the handle assembly of FIG. 5 before attachment with the handle assembly.
Figure 6B:
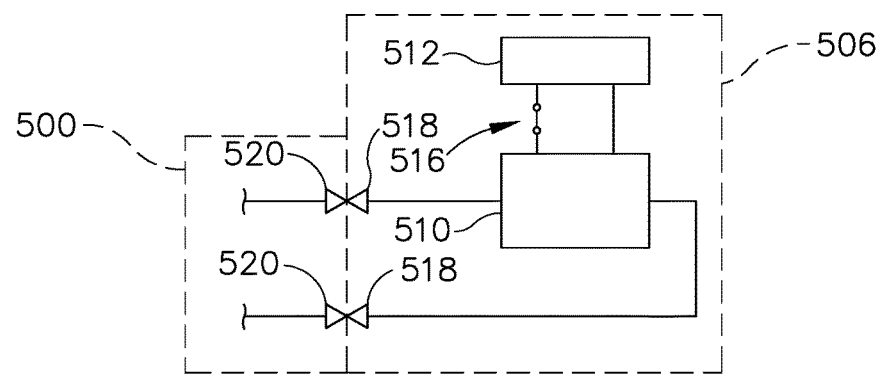
FIG. 6B depicts a schematic diagram of the power source attached with the handle assembly of FIG. 5.
Figure 6C:
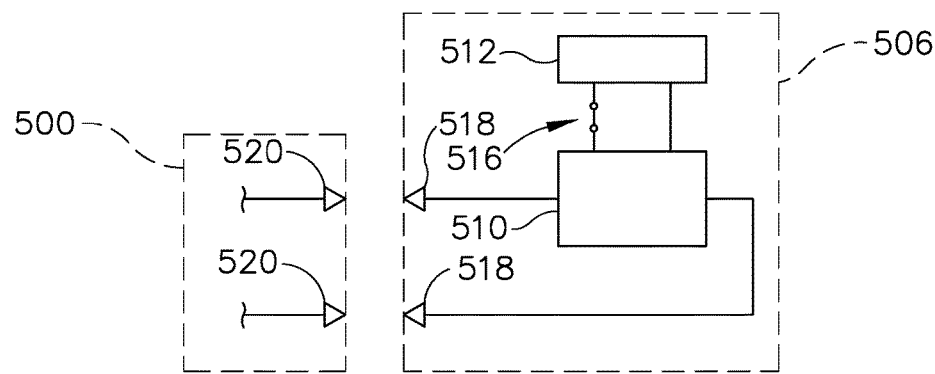
FIG. 6C depicts a schematic diagram of the power source detached from the handle assembly of FIG. 5 after attachment with the handle assembly.

FIGS. 6A-6C schematically illustrate battery unit (506) and a portion of instrument (500). Battery unit (506) may comprise a power drain (512) that automatically completes a circuit within battery unit (506) upon attachment to surgical instrument (500). Power drain (512) serves to slowly reduce the charge of battery unit (506) over time. Once battery unit (506) has been sufficiently drained, it may be disposed as non-hazardous waste, for example. Battery unit (506) includes an integral voltage source (510). In some versions, voltage source (510) comprises a lithium battery and comprises at least one cell selected from the group consisting of a CR123 cell and a CR2 cell. As is will be appreciated, any suitable voltage source may be used. Battery unit (506) further includes drain (512) that is electrically coupled to voltage source (510) when a switch (516) is closed. Battery unit (506) and surgical instrument (500) each comprise electrically conductive contacts (518, 520), respectively, that are placed into contact upon attachment of battery unit (506) to surgical instrument (500).

FIG. 6A illustrates battery in a non-attached position. Switch (516) is in an open state and voltage source (510) is in a fully charged condition. FIG. 6B illustrates battery unit (506) in an attached position. Conductive contacts (518) of battery unit (506) are in electrical communication with contacts (520) of surgical instrument (500), thereby allowing battery unit (506) to supply energy to circuit (514) (see FIG. 5). In the attached position, switch (516) transitions to the closed state to electrically couple voltage source (510) to power drain (512). Energy will flow from voltage source (510) through power drain (512) during operation of surgical instrument (500). In other words, power drain (512) will be draining the charge from voltage source (510) concurrently as battery unit (506) is supplying operational power to surgical instrument (500). As discussed in more detail below, a portion of surgical instrument (500) may physically interact with power drain (512) during attachment of battery unit (506) to surgical instrument (500) to transition switch (516) from the open state to the closed state. FIG. 6C illustrates battery unit (506) in a non-attached position. In the present example, switch (516) remains in the closed state to continue to drain the voltage source (510) even after battery unit (506) has been detached from surgical instrument (500).

Figure 7:
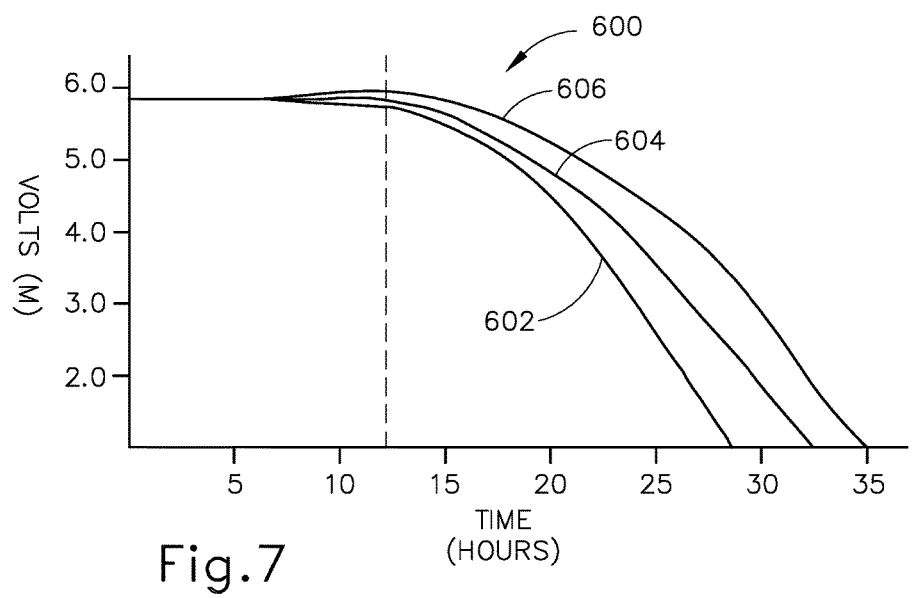
FIG. 7 depicts a graph of a voltage level of the power source of FIG. 5, as measured from a time of attachment with the handle assembly.

FIG. 7 is a graph (600) of the voltage level of battery unit (506) over time, as measured from the time of attachment to surgical instrument (500), in accordance with one non-limiting example. Graph (600) illustrates the voltage levels of a 6V cell of battery unit (506). Graph (600) is merely representative of one example of battery unit (506). As it will be appreciated, while graph (600) illustrates a 6 VDC power supply, battery unit (506) may supply any suitable voltage, such as 9 VDC, 12 VDC or 18 VDC, for example. As discussed in more detail below, battery unit (506) may comprise multiple cells arranged in a parallel and/or series configuration. Graph (600) includes three example discharge curves (602, 604, 606). As illustrated by first discharge curve (602), the voltage of power source (510) drops below 2.0 volts after around 28 hours. As illustrated by second discharge curve (604), the voltage of power source (510) drops below 2.0 volts after around 30 hours. As illustrated by third discharge curve (606), the voltage of power source (510) drops below 2.0 volts after around 33 hours. The overall shape of a discharge curve may depend upon, for example, the level of activity of surgical instrument (500) during the surgical procedure. For example, surgical instrument (500) associated with first discharge curve (602) was more heavily used during the surgical procedure than surgical instrument (500) associated with third discharge curve (606).

Figure 8:
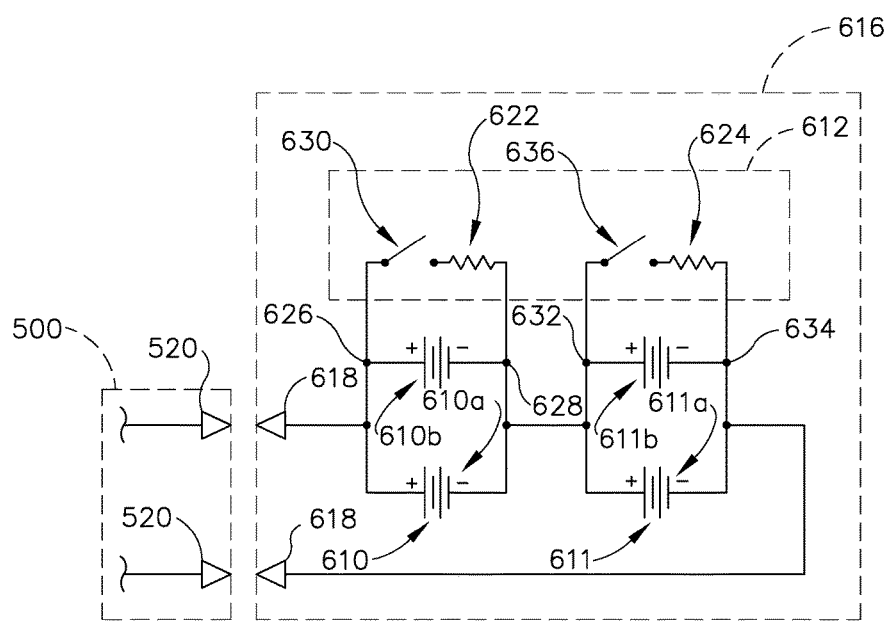
FIG. 8 depicts a simplified circuit diagram of the surgical instrument of FIG. 5 including an exemplary power drain.

In some versions, a resistive element is used to reduce the power level of the voltage source. FIG. 8 is a simplified circuit diagram of a battery unit (616) comprising a power drain (612). Battery unit (616) may be attached to surgical instrument (500), for example, via its contacts (618). In this example, battery unit (616) comprises a first grouping of cells (610) and a second grouping of cells (611). By way of example only, groupings of cells (610, 611) may comprise lithium batteries. Groupings of cells (610, 611) may each have a plurality of separate cells (610a, 610b, 611a, 611b) arranged in a parallel formation. For example, groupings of cells (610, 611) may each be 6 VDC and arranged in a series configuration to produce 12 VDC at contacts (618) of battery unit (616) when fully charged. Cells (610a, 610b, 611a, 611b), however, may be electrically connected to one another in series or parallel or any other combination thereof.

In the present example, power drain (612) comprises a first resistive element (622) and a second resistive element (624). In some versions, battery unit (616) comprises multiple power drains (612), each having more or less than two resistive elements or other circuitry. In the illustrated example, resistive element (622) is coupled across an anode (626) and a cathode (628) of grouping of cells (610) through a switch (630). Resistive element (624) is also coupled across an anode (632) and a cathode (634) of grouping of cells (611) through a switch (636). Switches (630, 636) are configured to be closed upon attachment of battery unit (616) to surgical instrument (500) in order to initiate the draining of groupings of cells (610, 611).

The value of the resistive elements utilized by power drain (612) may vary based on implementation. In some versions, resistive element (622) has a resistance in the range of about 90 ohms to about 110 ohms, or more particularly, in the range of about 97 ohms to about 104 ohms, or even more particularly at a value of 102.9 ohms with a power rating of 1 watt. The determination of the necessary resistance may be based at least partially on the capacity of the voltage source, the voltage level of the voltage source, and the desired temporal length of the drainage curve. For example, in some versions the battery capacity of grouping of cells (610) is 1400 mAh, the voltage level is 6 VDC, and the target drain time is 24 hours. Diving 1400 mAh by 24 hours yields a current of 0.0582 A. Using Ohm's law, 6 V divided by 0.582 A yields a resistance of 102.9 ohms. With a current of 0.583 and a resistance of 102.9 ohms, the power dissipated by the resistor is 0.350 W. As is to be appreciated, different voltage levels, battery capacities, and desired time of discharge will result in different resistance values.

Figure 9:
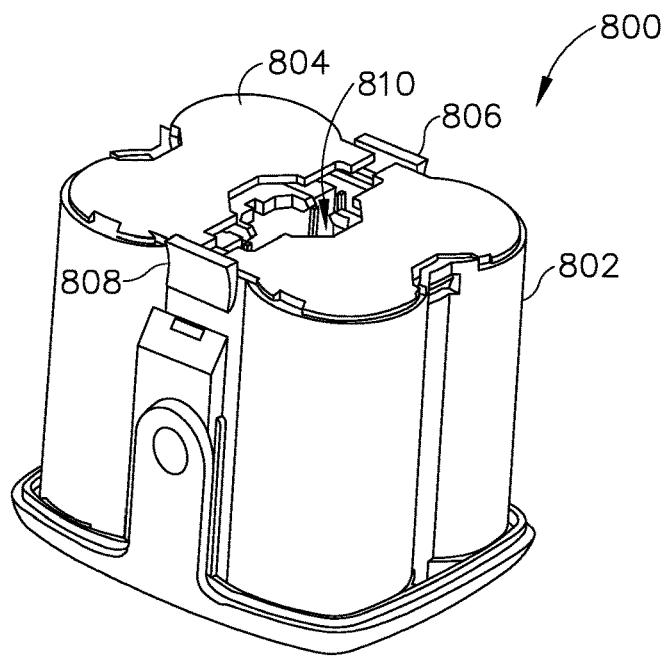
FIG. 9 depicts a perspective view of the power source of FIG. 5 in the form of an exemplary battery unit.
Figure 10:
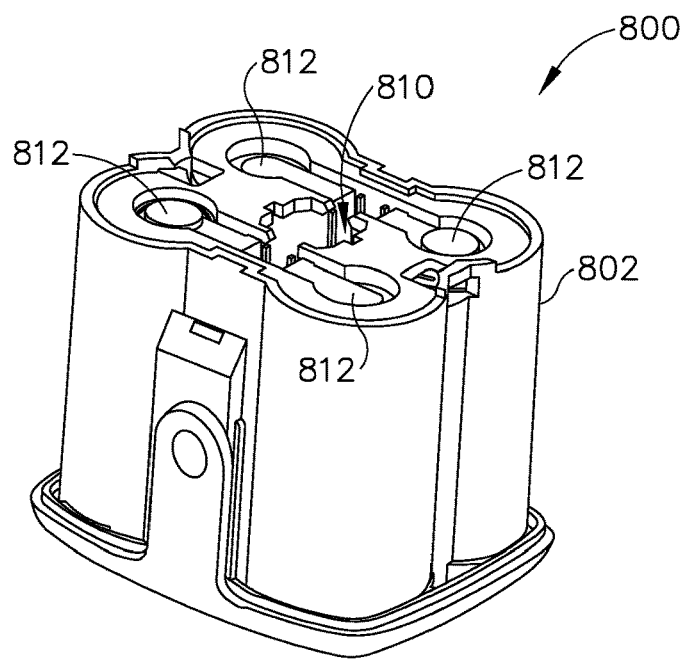
FIG. 10 depicts another perspective view of the battery unit of FIG. 9, with a cap removed from the battery unit.
Figure 11:
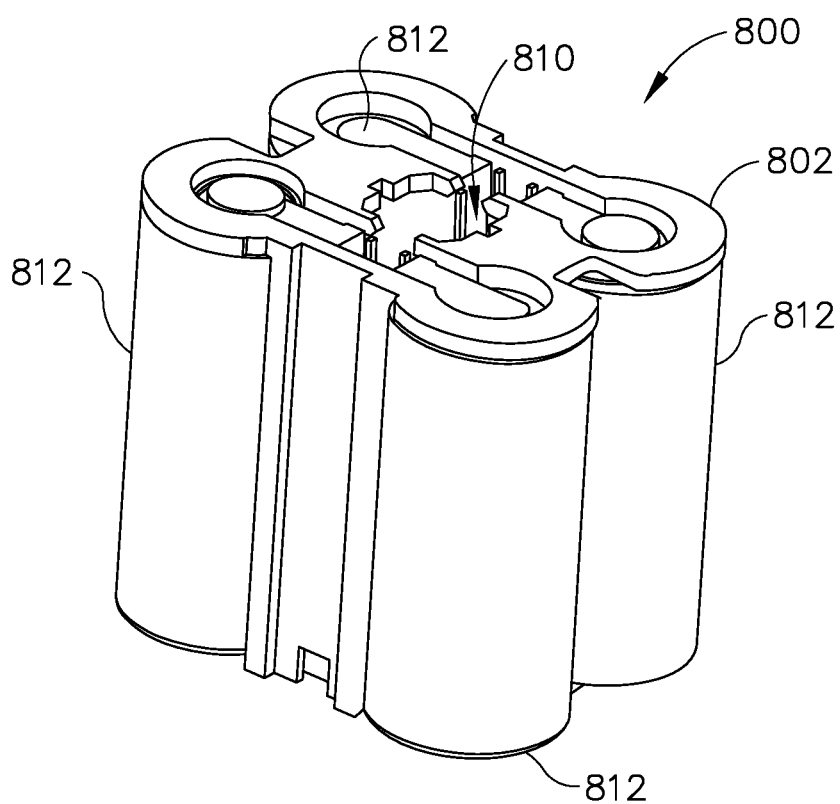
FIG. 11 depicts yet another perspective view of the battery unit of FIG. 9, with the cap and a casing removed from the battery unit.

FIGS. 9-11 are perspective views of a battery unit (800) implementing the circuitry of battery unit (616) shown in FIG. 8. Battery unit (800) comprises a casing (802) defining an interior cavity (810). While interior cavity (810) is illustrated in a central portion of casing (802), it is to be appreciated that internal cavity (810) may be positioned in any suitable location. Casing (802) is covered by a cap (804) that is secured to casing (802) utilizing one or more mechanical latches (806, 808). FIG. 10 illustrates battery unit (800) with cap (804) removed to show a plurality of cells (812) within. Any suitable number and/or type of cells (812) may be used. For example, CR123 and/or CR2 cells may be used. FIG. 11 illustrates battery unit (800) with a portion of casing (802) removed to reveal cells (812).

Figure 12A:
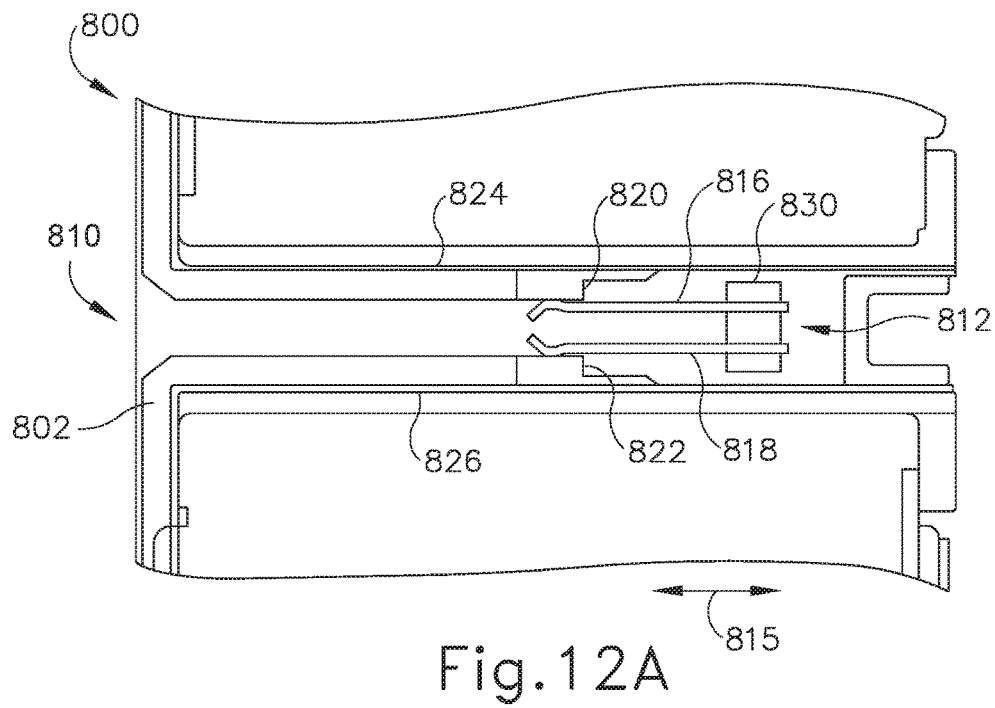
FIG. 12A depicts a cross-sectional side view of another exemplary power drain in an open position.
Figure 12B:
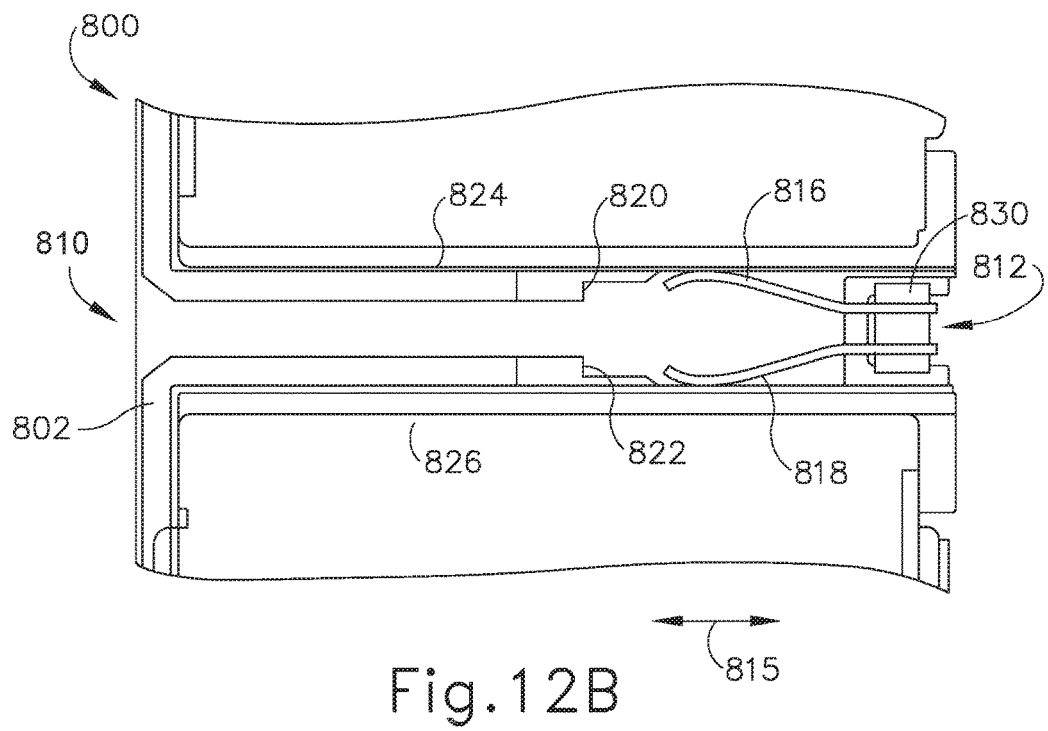
FIG. 12B depicts a cross-sectional side view the power drain of FIG. 12A in a closed position.

FIGS. 12A and 12B illustrate cross-sectional views of an exemplary battery unit (800) including a translatable power drain (812). Power drain (812) may be positioned within interior cavity (810) and may be translatable within interior cavity (810) in the directions of arrow (815). FIG. 12A shows power drain (812) in an open position and FIG. 12B shows power drain (812) in a closed state. Power drain (812) may comprise at least two contacts (816, 818). When power drain (812) is in the open position, a portion of contacts (816, 818) may touch a non-conductive portion of casing (802), such as fingers (820, 822). In the present example, contacts (816, 818) are resiliently biased to exert a force against fingers (820, 822) in order to resist movement of drain (812) in the direction of arrows (815). Also, fingers (820, 822) may define one or more protrusions or stepped down portions, as shown in FIGS. 12A and 12B. Battery unit (800) of the present example also comprises electrodes (824, 826). Electrodes (824, 826) may each be electrically coupled to a cathode or an anode of cells contained within battery unit (800). In the closed position (FIG. 12B), contacts (816, 818) are in electrical connection with electrodes (824, 826), thereby allowing the voltage source to discharge through power drain (812). As discussed in more detail below, power drain (812) may be transitioned from the open position to the closed position upon attachment of battery unit (800) to surgical instrument (500).

Figure 13:
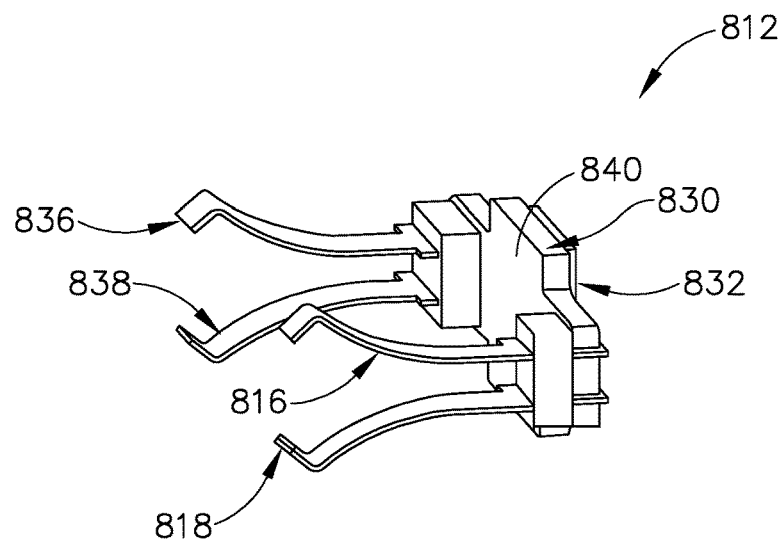
FIG. 13 depicts a perspective view of the power drain of FIG. 12A.

FIG. 13 is a perspective view of power drain (812) in accordance with one non-limiting example. Contacts (816, 818) of drain (812) are coupled to a base portion (830) of drain (812). Similarly, contacts (836, 838) of drain (812) are coupled to base portion (830) of drain (812). According to various examples, contacts (816, 818) may be electrically connected to one another via a resistive element (not shown) mounted to a circuit board (832). Similarly, contacts (836, 838) may be electrically connected to one another via a resistive element mounted to circuit board (832). As illustrated, contacts (816, 818, 836, 838) may have a bend or curvature to resiliently bias contacts (816, 818, 836, 838) toward an outward position when inwardly compressed. Additionally, in the present example, distal end of each of contacts (816, 818, 836, 838) has an inwardly turned section. Base portion (830) comprises a contacting surface (840) that engages surgical instrument (500) when battery unit (800) is attached to surgical instrument (500). Through this engagement, battery drain (812) may be translated relative to casing (800).

Figure 14:
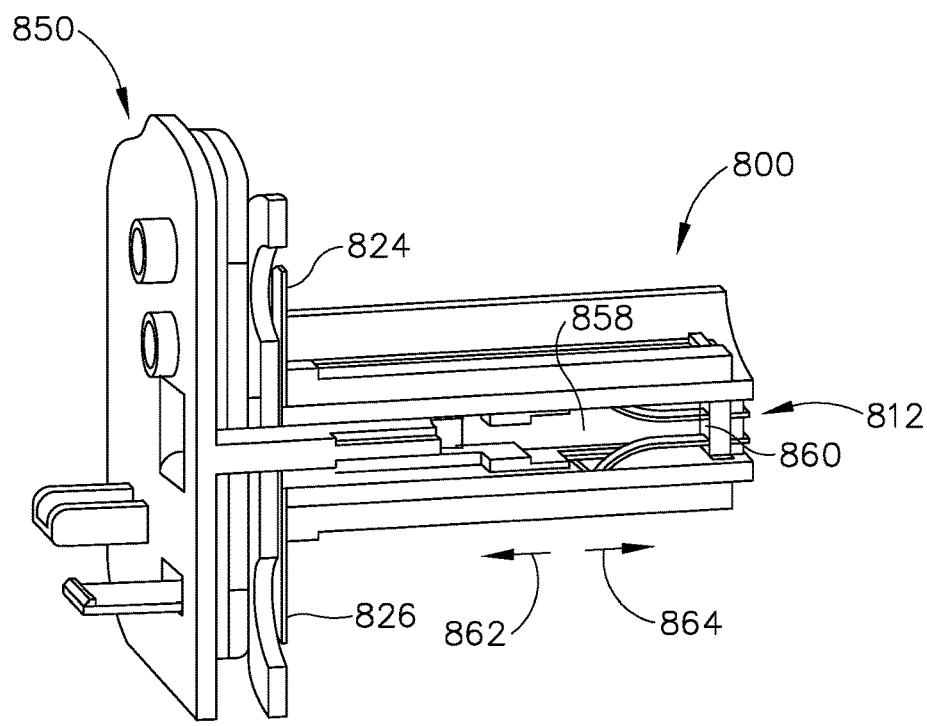
FIG. 14 depicts another exemplary battery unit attached to an exemplary dock of a handle assembly with various components omitted for clarity.

FIG. 14 illustrates battery unit (800) attached to a battery dock (850). For clarity, various components have been removed. Referring now to FIGS. 12A-14, battery dock (850) comprises a protruding member (858) that is sized to be received by cavity (810) (see FIG. 9) of battery unit (800). Prior to attachment, power drain (812) is in the open position (FIG. 12A). During attachment of battery unit (800) to battery dock (850), protruding member (858) is inserted into the cavity (810) and battery unit (800) is moved relative to battery dock (850) in the direction indicated by arrow (862). Eventually distal end (860) of protruding member (858) contacts contacting surface (840) of power drain (812). As the operator continues to attach battery unit (800), power drain (812) translates relative to casing (802) in the direction indicated by arrow (864) and moves to the closed position (see FIG. 12B). In this closed position, battery unit (800) commences to slowly drain. When the battery unit (800) is removed from battery dock (850), power drain (812) may remain in the position shown in FIG. 12B. In this way, the cells (not shown) of battery unit (800) may drain any remaining charge across a resistive element either before or during disposal.

Additional details regarding surgical instruments and battery units that may be combined with the above teachings are described in U.S. Pub. No. 2012/0071711, entitled "Surgical Instruments and Batteries for Surgical Instruments," published Mar. 22, 2012, issued as U.S. Pat. No. 9,289,212 on Mar. 22, 2016, the disclosure of which is incorporated by reference herein; and U.S. Pat. No. 8,632,525, entitled "Power Control Arrangement for Surgical Instrument and Batteries," filed Sep. 17, 2010, the disclosure of which is incorporated by reference herein. Of course, the foregoing teachings may also be readily combined with the teachings of any other references that are cited herein.

III. Exemplary Surgical Instrument with a Delayed Battery Drain

While the above surgical instruments (10, 500) provide for power sources (116, 510) having battery units (118, 506, 616, 800) that include power drains (512, 612, 812), it will be appreciated that present and future improvements to surgical instruments (10, 500) and related surgical procedures may place additional demand on battery units (118, 506, 616, 800). Such surgical instruments (10, 500) may not retain sufficient electrical power charge during these surgical procedures, particularly in combination with power drains (512, 612, 812) simultaneously in use. It may therefore be desirable to provide a surgical instrument (1000) with a battery unit (1010) having a power drain (1012) that is configured to delay draining of battery unit (1010) until after the surgical procedure is complete. Thereby, surgical instrument (1000) will more likely have sufficient electrical power to perform the surgical procedure and later drain for disposing battery unit (1010) as non-hazardous waste. It should be understood that that the features discussed below may be readily incorporated into surgical instruments (10, 500) discussed above. To this end, like numbers indicate like features described above in greater detail.

A. Exemplary Battery Drain using Microprocessor

Figure 15:
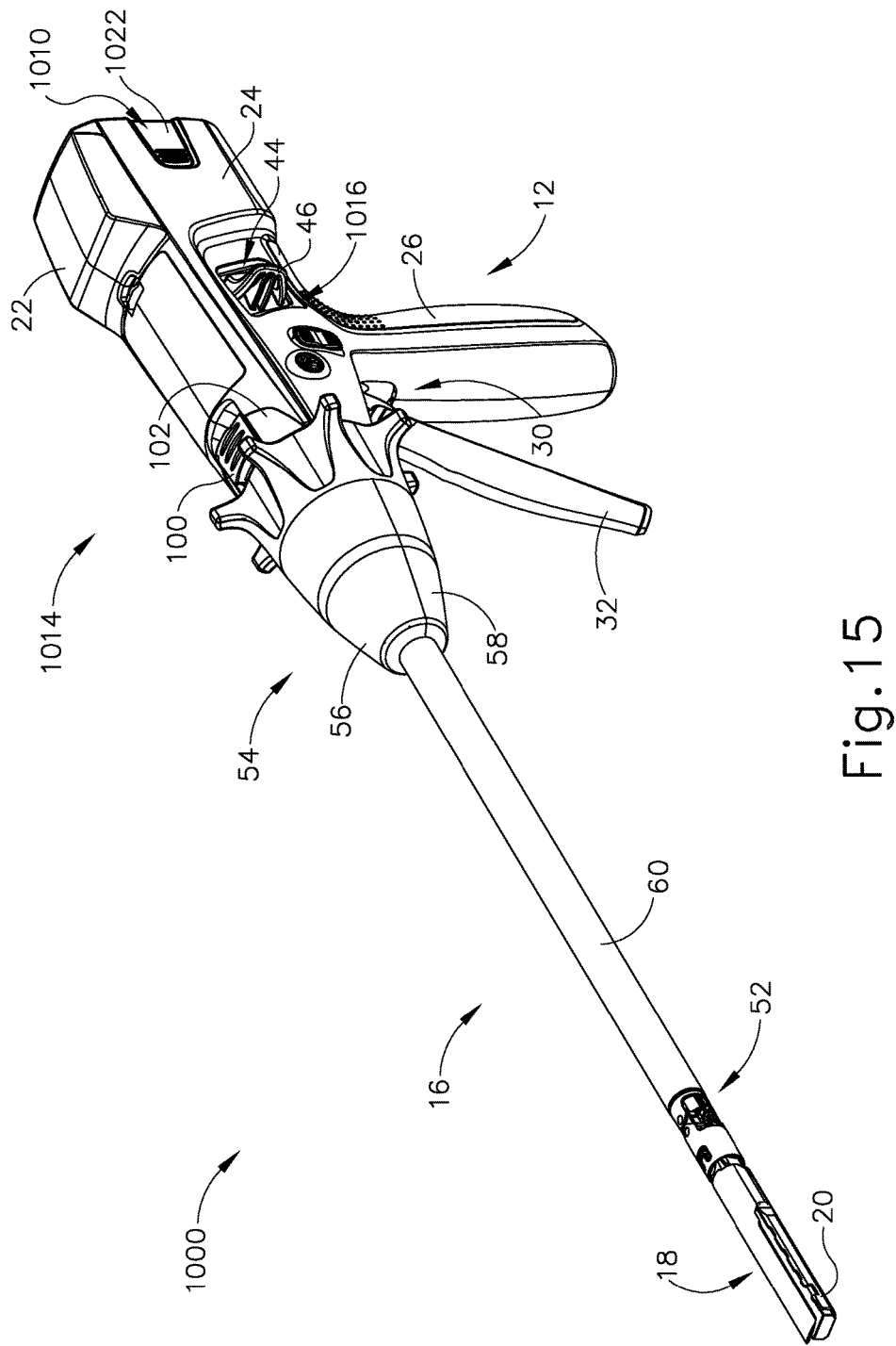
FIG. 15 depicts a perspective view of yet another exemplary surgical stapling instrument having a shaft assembly and a handle assembly.
Figure 16:
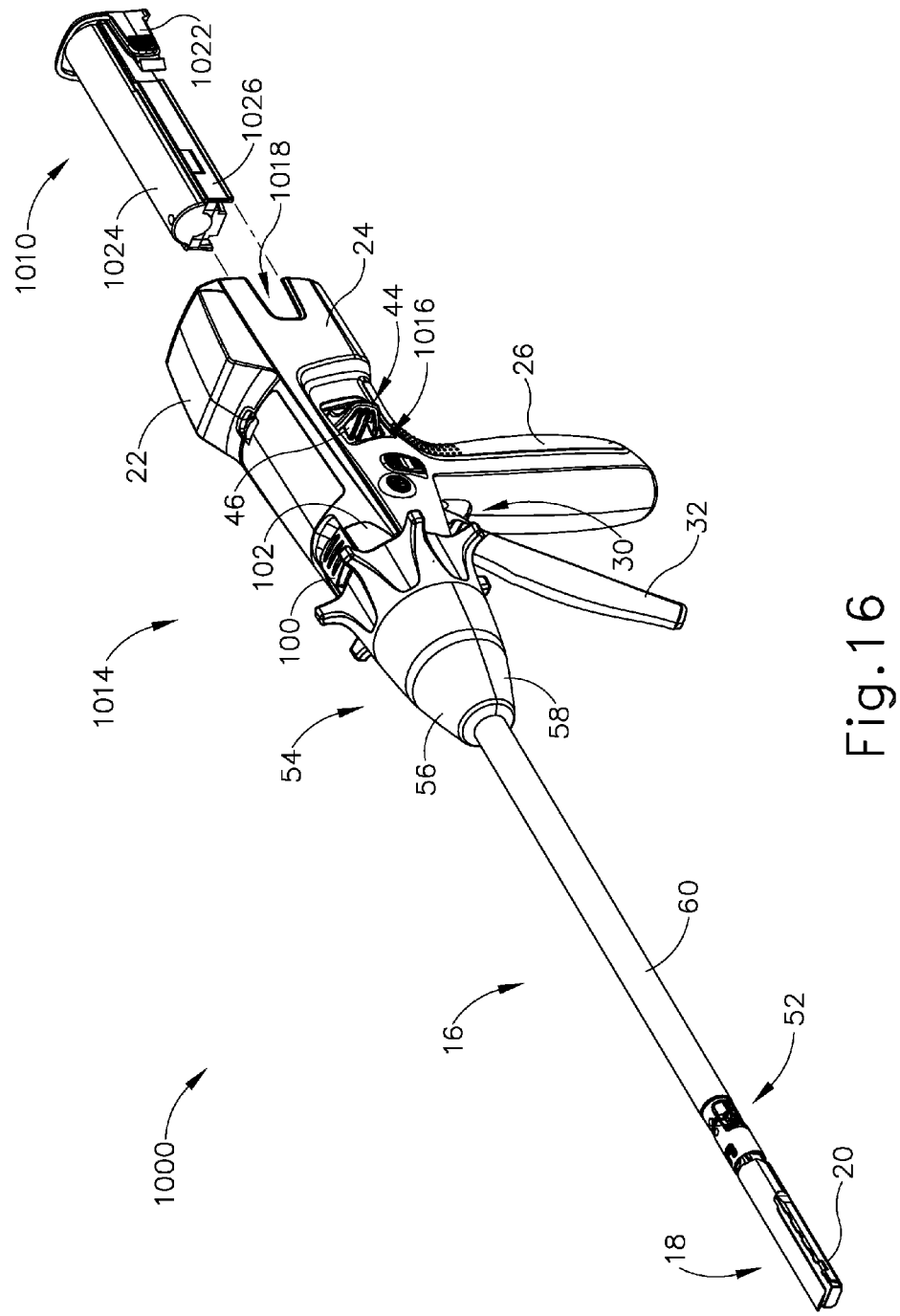
FIG. 16 depicts a partially exploded perspective view of the instrument of FIG. 15, showing a power source detached from the handle assembly.
Figure 17:
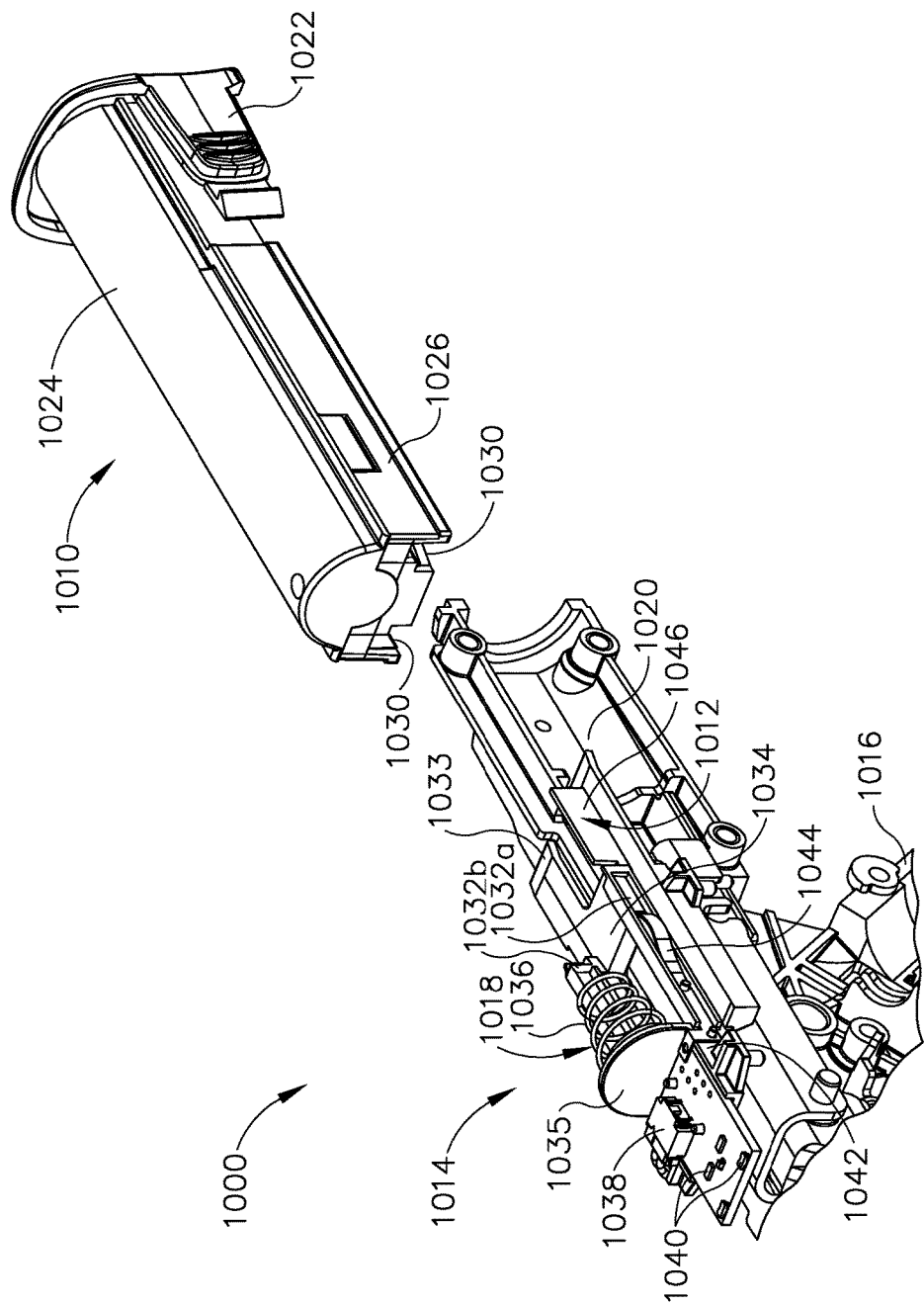
FIG. 17 depicts an enlarged partially exploded perspective view of the instrument and power source of FIG. 16 with various components omitted for clarity.

FIGS. 15-17 show exemplary surgical instrument (1000) having shaft assembly (16) and a handle assembly (1014). Like handle assembly (11) (see FIG. 1) discussed above, handle assembly (1014) is configured to operatively couple with shaft assembly (16) and operate end effector (18) via closure system (30). Handle assembly (1014) further includes a handle (1016) having a battery dock (1018) that is configured to receive a power source, such as battery unit (1010). Thereby, battery unit (1010) mechanically connects with handle (1016) and electrically connects with handle assembly (1014) and shaft assembly (16) in order to provide electrical power to closure system (30) and end effector (18) for use during the surgical procedure.

Battery unit (1010) is separable relative to handle assembly (1014), which may be reusable. For example, FIGS. 16-17 show battery unit (1010) being inserted into battery dock (1018) for installation, causing clips (1022) to engage with cooperating dock detents (not shown), which both secure battery unit (1010) within battery dock (1018) and provide feedback to the operator that battery unit (1010) is properly installed within battery dock (1018). Of course, it will be appreciated that alternative structures for securing battery unit (1010) within battery dock (1018) may be similarly used in alternative versions.

FIG. 17 shows additional details of battery unit (1010) and battery dock (1018) mounted on a dock frame (1020) of handle assembly (1014) prior to installation. Battery unit (1010) includes a battery cover (1024) attached to a battery base (1026), which collectively contain a plurality of batteries (1028) (see FIG. 19) therein. Battery base (1026) also includes a pair of opposing, elongated guide slots (1030) longitudinally extending along a bottom of battery base (1026). Battery dock (1018) includes a left elongated guide member (1032a) parallel with and offset from a right elongated guide member (1032b). Guide members (1032a, 1032b) are configured to be received within guide slots (1030). As such, guide slots (1030) and guide members (1032a, 1032b) cooperatively guide battery unit (1010) longitudinally as battery unit (1010) slides in and out of guide dock (1018) during insertion and removal of battery unit (1010). In addition, battery dock (1018) further includes a ramp (1033) that is configured to guide battery unit transversely upward onto a saddle (1034), which is configured to support battery unit (1010) during use of surgical instrument (1000).

Battery dock (1018) further includes a battery bulkhead (1035) positioned at a distal end of guide members (1032a, 1032b). Battery bulkhead (1035) has a spring (1036) extending proximally therefrom in order to bias battery unit (1010) thereagainst and urge the battery unit (1010) proximally for removal. Battery dock (1018) also includes a dock circuit board (1038) that is powered by battery unit (1010) during use. In the present example, dock circuit board (1038) has a plurality of indicators in the form of LED lights (1040) connected thereto and configured to indicate to the operator an operational status of surgical instrument (1000), such as a remaining amount of electrical power in battery unit (1010), operative connection of battery unit (1010) with handle assembly (1014), and/or operative connection of shaft assembly (16) with handle assembly (1014). It will be appreciated; however, that dock circuit board (1038) and LED lights (1040) may be alternatively configured to indicate other forms of status information regarding surgical instrument (1000) to the user. Moreover, it will be appreciated that dock circuit board (1038) may include additional electronics that are configured to provide clinical function to surgical instrument (1000). As such, the invention described herein is not intended to be limited to the dock circuit board (1038) described herein. It should also be understood that LED lights (1040) are merely illustrative examples, such that any other suitable form(s) of indicator(s) may be used in addition to or in lieu of LED lights (1040).

Figure 18:
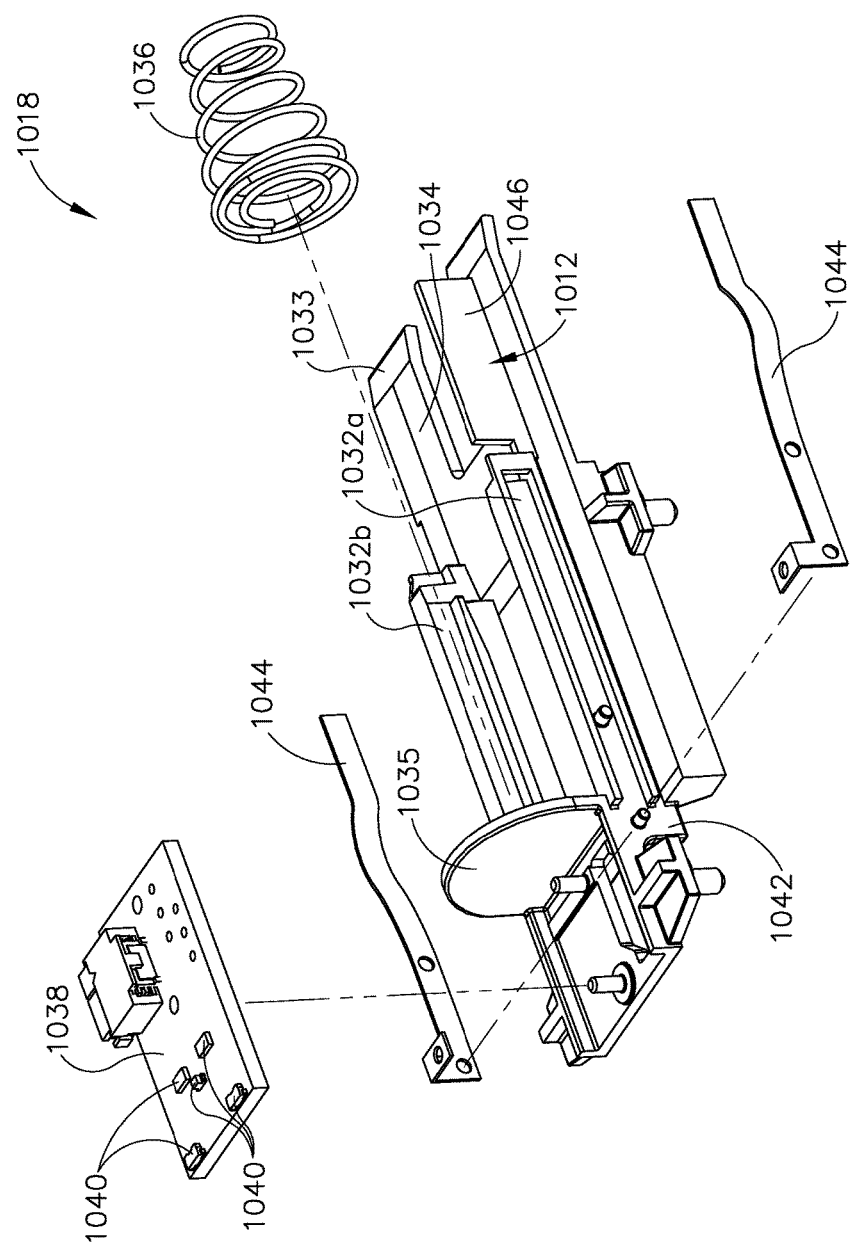
FIG. 18 depicts a perspective view of a battery dock of the instrument of FIG. 15.

FIG. 18 shows battery dock (1018) in greater detail having a dock chassis (1042) supporting guide members (1032a, 1032b), ramp (1033), saddle (1034), battery bulkhead, and circuit board (1038) as described above. In addition, battery dock (1018) has a pair of opposing, elongated board contacts (1044) extending respectively along guide members (1032a, 1032b). A distal end of each board contact (1044) electrically connects to dock circuit board (1038), whereas a proximal end of each board connect (1044) is configured to engage battery unit (1010) for communicating electrical power from battery unit (1010) to dock circuit board (1038). Furthermore, battery dock (1018) has an elongated protruding member, such as a switch arm (1046), extending upwardly from saddle (1034) and proximally from left guide member (1032a). Switch arm (1046) is configured to engage a portion of drain (1012) for operating drain (1012) as will be discussed below in additional detail.

As shown in FIGS. 19-20, battery unit (1010) includes battery cover (1024), battery base (1026), and three batteries (1028) aligned in series within battery cover and base (1024, 1026). Battery unit (1010) further includes a battery circuit (1048) having a power circuit (1050) and a power drain circuit (1052). Battery circuit includes (1048) a distal conductive member (1054) and a proximal conductive member (1056). Distal conductive member (1054) includes a power cathode contact (1058) and a discharge cathode contact (1060), while proximal conductive member (1054) similarly includes a power anode contact (1062) and a discharge anode contact (1064). Thus, power cathode and anode contacts (1058, 1062) are part of power circuit (1050), whereas discharge cathode and anode contacts (1060, 1064) are part of power drain circuit (1052). Power cathode and discharge cathode contacts (1058, 1060) and power anode and discharge anode contacts (1062, 1064) are configured to electrically connect to a cathode (1066) and an anode (1068) of a collection of batteries (1028). Power circuit (1050) provides electrical power to dock circuit board (1038) when battery unit (1010) operatively connects with battery dock (1018). In contrast, power drain circuit (1052) is configured to selectively close to drain batteries (1028).

Figure 21:
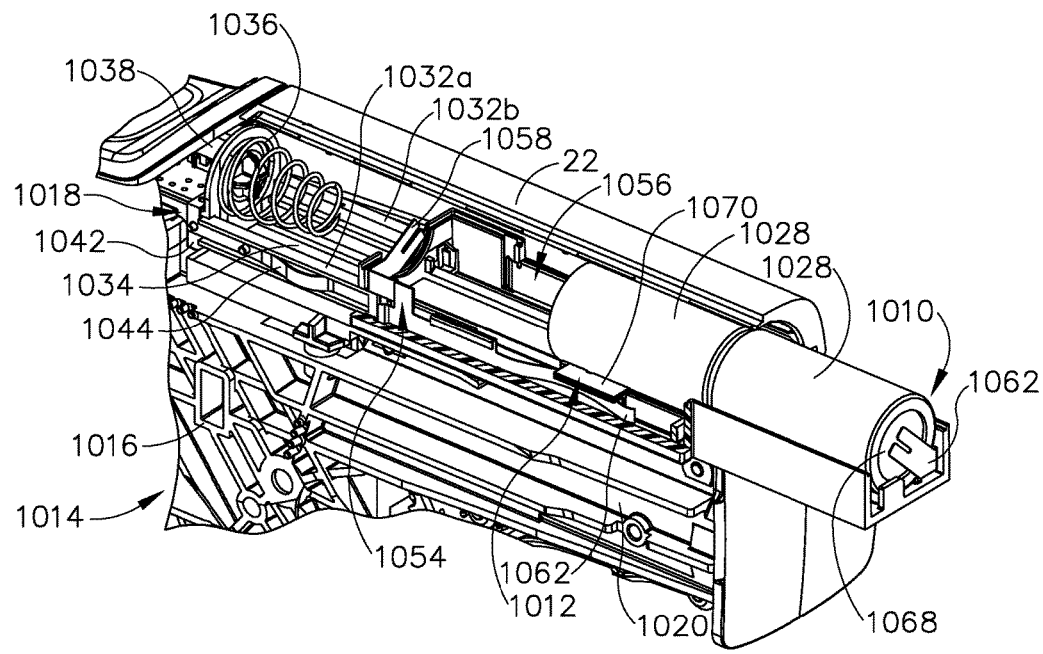
FIG. 21 depicts a rear perspective sectional view of the instrument of FIG. 15 with various components omitted for clarity.
Figure 22:
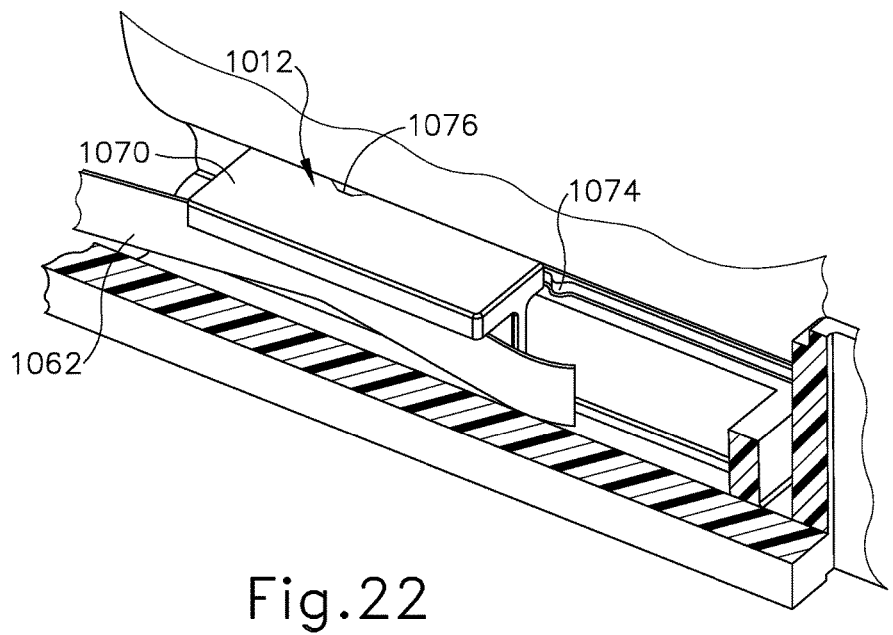
FIG. 22 depicts an enlarged rear perspective sectional view of the instrument of FIG. 15 with various components omitted for clarity.

To this end, power drain (1012) includes a discharge switch (1070) and power drain circuit (1052) having a discharge circuit board (1072) to, first, selectively connect batteries (1028) to power drain circuit (1052); second, delay drain of batteries (1028); and, third, initiate and complete drain of batteries (1028). In the example shown in FIGS. 21-22, discharge switch (1070) is translatably mounted within battery base (1026) to slide proximally from a blocker position to a released position. In the blocker position, discharge switch (1070) covers discharge cathode contact (1060) prior to installation with handle assembly (1014) in order to provide a physical barrier to electrically connecting batteries (1028) to drain circuit (1052). Discharge cathode contact (1060) is thus held in an open position, but biased against discharge switch (1070) toward a closed position. However, inserting battery unit (1010) into battery dock (1018) causes switch arm (1046) to engage discharge switch (1070) and slide discharge switch (1070) to the released position, thereby releasing discharge cathode contact (1060) and connecting batteries (1028) to power drain circuit (1052). Battery base (1026) and discharge switch (1070) respectively have cooperating base and switch detents (1074, 1078) to secure discharge switch (1070) in the released position and inhibit discharge switch (1070) from returning to the blocker position. By way of example, FIGS. 23A and 24A show discharge cathode contact (1060) held away from connection with power drain circuit (1052) in the open position, with discharge switch in the blocker position, prior to installation. In contrast, FIGS. 23B and 24B show discharge cathode contact (1060) biased against power drain circuit (1052) in the closed position, with discharge switch in the released position, after installation.

FIG. 25 schematically shows the exemplary power drain circuit (1052) with discharge circuit board (1072) for delaying and initiating drain of batteries (1028). Drain circuit (1052) further includes a resistor element, such as a resistor (1078); a switch element, such as a metal-oxide semiconductor field-effect ("MOSFET") transistor (1080); and a controller, such as the collection of a microprocessor (1082a), Hall effect sensor (1082b), and opto-isolator (1082c). In the present example, drain circuit (1052) is configured to delay draining electrical power across resistor (1078) until battery unit (1010) is removed from battery dock (1018).

With respect to controller (1082a, 1082b, 1082c), Hall effect sensor (1082b) is configured to sense when battery unit (1010) is removed from the battery dock (1018) and communicate the sensed removal to microprocessor (1082a). It will be appreciated that various structures, mechanical, electrical, and magnetic, may be used to communicate removal to microprocessor (1082a). For example, battery dock (1018) may include a magnet (not shown) in proximity to Hall effect sensor (1082b) such that a reduction in magnetic field upon removal of Hall effect sensor (1082b) from battery dock (1018) causes Hall effect sensor (1082b) to communicate this removal to microprocessor (1082a). Given alternative methods for sensing removal with a portion (1082b) of controller (1082a, 1082b, 1082c), alternative sensors may be so used. In addition, the Hall effect sensor (1082b) may alternatively be any form of proximity sensor, such as a reed switch microswitch, configured to sense removal thereof.

Microprocessor (1082a) is connected to MOSFET transistor (1080) via opto-isolator (1082c). Opto-isolator (1082c) is configured to pass a discharge signal from microprocessor (1082a) to MOSFET transistor (1080) while electrically isolating MOSFET transistor (1080) and resistor (1078) from microprocessor (1082a). MOSFET transistor (1080) acts as a switch that is configured to selectively electrically connect cathode (1066) to anode (1068) across resistor (1078). Prior to receiving the discharge signal, MOSFET transistor (1080) maintains an open circuit across resistor (1078) to prevent electrical power from cathode (1066) from flowing through resistor (1078). After receiving the discharge signal, MOSFET transistor (1080) closes the circuit across resistor (1078) to direct electrical power from cathode (1066) through resistor (1078) and effectively drain batteries (1028) across resistor (1078). Thereby, draining of batteries (1028) by power drain circuit (1052) is delayed until removal of battery unit (1010) from battery dock (1018). FIG. 25 shows two such drain circuits (1052) for two sets of batteries (1028). However, it will be appreciated that more or less drain circuits (1052) may be so used for draining the batteries (1028).

Figure 26:
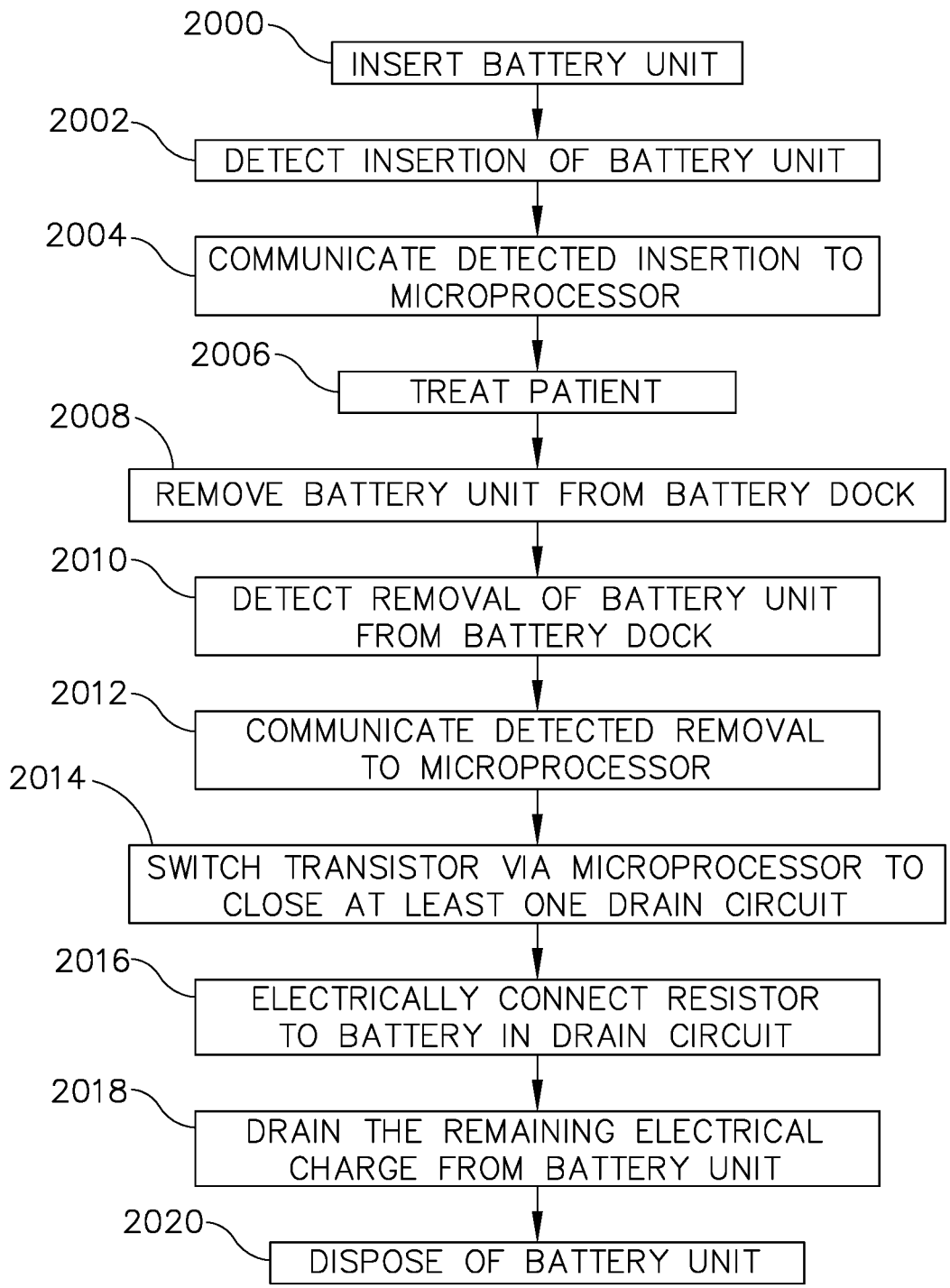
FIG. 26 depicts a flow chart showing an exemplary use of the power drain circuit of FIG. 25 with a surgical instrument.

FIG. 26 shows a flow chart of an exemplary use of surgical instrument (1000) having power drain circuit (1052) in relation to FIGS. 16-17, 21, and 25-26. The user inserts battery unit (1010) into battery dock (1018) to operatively connect battery unit (1010) to handle assembly (1014) and shaft assembly (16), as shown in block (2000). As such, switch arm (1046) directs discharge switch (1070) from the blocker position to the released position, and discharge cathode contact (1060) moves from the open position to the closed position to connect batteries (1028) to drain circuit (1052). The insertion of battery unit (1010) in battery dock (1018) is thus detected, as shown in block (2002). At approximately the same time, Hall effect sensor (1082b) communicates the insertion to microprocessor (1082a), as shown in block (2004). Microprocessor (1082a) prevents MOSFET transistor (1080) from connecting resistor (1078) across cathode (1066) and anode (1068) while the user performs the surgical procedure on the patient with surgical instrument (1000), as shown in block (2006).

After treatment, the user removes battery unit (1010) from battery dock (1018), as shown in block (2008). Hall effector sensor (1082b) detects removal of battery unit (1010) from battery dock (1018), as shown in block (2010); and communicates removal to microprocessor (1082a), as shown in block (2012). Microprocessor (1082a) then sends a discharge signal to MOSFET transistor (1080) via opto-isolator (1082c) in order to close power drain circuit (1052) with resistor (1078) between cathode and anode (1066, 1068), as shown in block (2014). Closing drain circuit (1052) directs electrical power through resistor (1078), as shown in block (2016); and thereby effectively drains a remaining portion of electrical power from batteries (1028), as shown in block (2018). In other words, drain (1012) delays draining electrical power from battery unit (1010) until battery unit (1010) is removed from battery dock (1018). Drained battery unit (1010) may then be properly disposed of, as shown in block (2020).

B. Exemplary Battery Drain Using Timer

Figure 27:
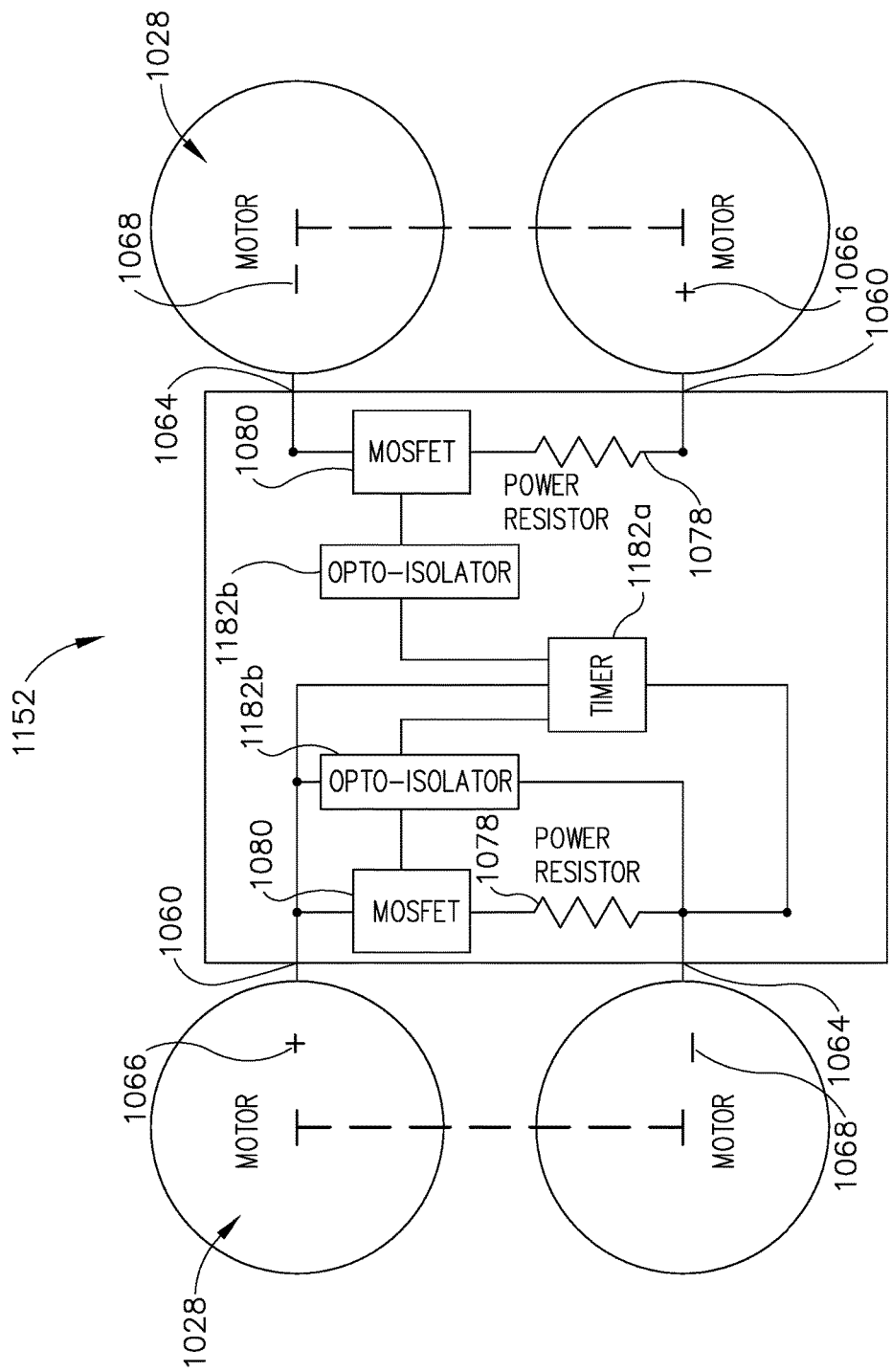
FIG. 27 depicts a schematic circuit diagram of an exemplary alternative power drain circuit.

FIG. 27 shows an exemplary alternative power drain circuit (1152) that may be readily incorporated into instrument (1000) in place of power drain circuit (1052) described above. In particular, FIG. 27 schematically shows power drain circuit (1152) of drain (1112) with a discharge circuit board (1172) for delaying and initiating drain of batteries (1028). Power drain circuit (1152) of this example further includes a resistor element, such as resistor (1078); a switch element, such as a metal-oxide semiconductor field-effect ("MOSFET") transistor (1080); and a controller, such as the collection of a timer (1182a) and an opto-isolator (1182b). In the present example, power drain circuit (1152) is configured to delay draining electrical power across resistor (1078) until a predetermined amount of time has passed since electrical power was initially discharged from batteries (1028).

With respect to collective controller (1182a, 1182b), timer (1182a) is configured to sense when batteries (1028) initially discharge electrical power after insertion of battery unit (1010) in battery dock (1018); and timer (1182a) begins computing passage of time from the initial discharge. In addition to timer (1182a), alternative examples may further include the timer in the form of an analog timer circuit, a digital timer, a microprocessor with a timer program, or other timing device. Given alternative methods for computing the passage of time, alternative timers may be so used. While the predetermined amount of time may be any desirable amount of time, one example of a desirable amount of time is an amount of time as long as the predicted time for completing the surgical procedure. Of course, other desirable times may be programmed into timer (1182a). In any case, timer (1182a) communicates the discharge signal toward MOSFET transistor (1080) after the passage of the predetermined amount of time.

Timer (1182a) is connected to MOSFET transistor (1080) via opto-isolator (1182b). Opto-isolator (1182b) is configured to pass the discharge signal from timer (1182a) to MOSFET transistor (1080) while electrically isolating MOSFET transistor (1080) and resistor (1078) from timer (1182a). Prior to receiving the discharge signal, MOSFET transistor (1080) maintains an open circuit across resistor (1078) to prevent electrical power from cathode (1066) from flowing through resistor (1078). After receiving the discharge signal from timer (1182a), MOSFET transistor (1080) closes the circuit across resistor (1078) to direct electrical power from cathode (1066) through resistor (1078) and effectively drain batteries (1028) across resistor (1078). Thereby, draining of batteries (1028) by power drain circuit (1152) is delayed until the predetermined amount of time has passed from initial discharge of electrical power. FIG. 27 shows two such power drain circuits (1152) for two sets of batteries (1028); however, it will be appreciated that more or less power drain circuits (1152) may be so used for draining the batteries (1028).

Figure 28:
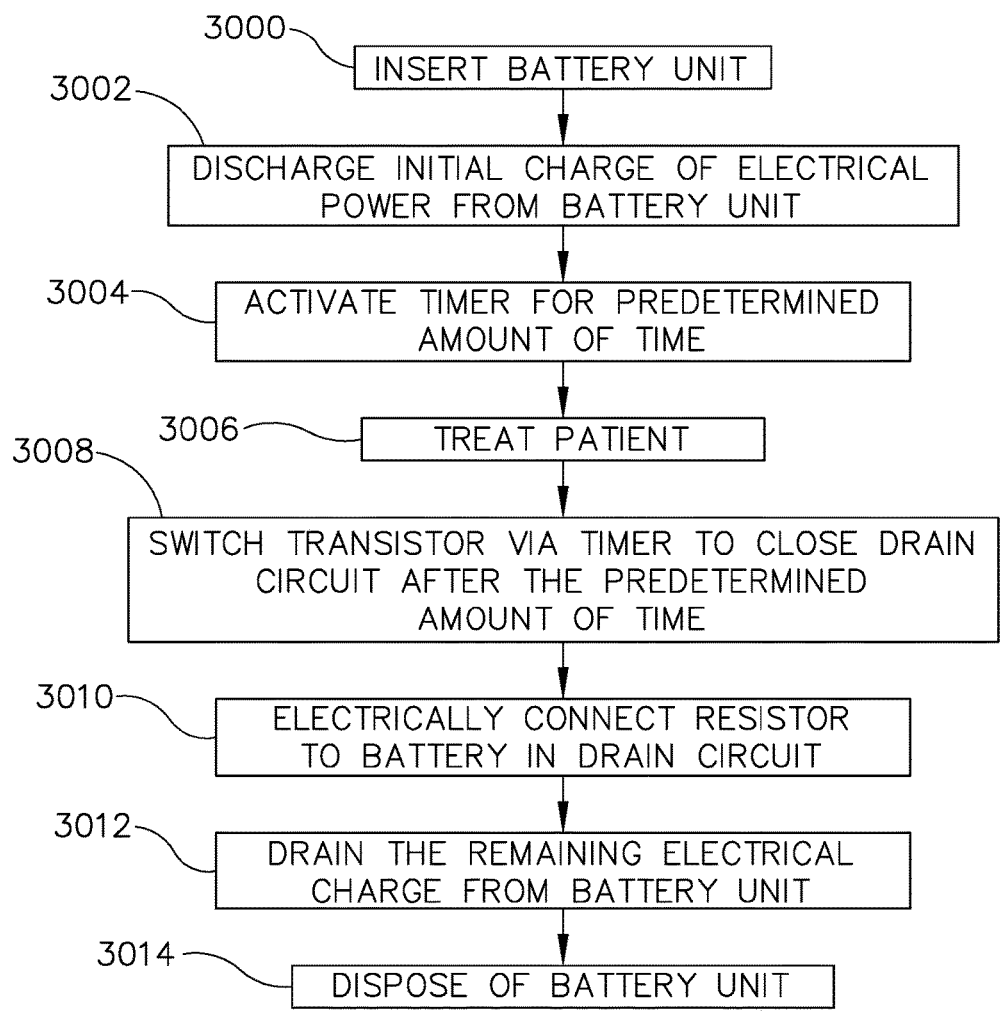
FIG. 28 depicts a flow chart showing an exemplary use of the power drain circuit of FIG. 27 with a surgical instrument.

FIG. 28 shows a flow chart of an exemplary use of surgical instrument (1000) having drain circuit (1152) in relation to FIGS. 16-17, 21, and 27-28. The user inserts battery unit (1010) into battery dock (1018) to operatively connect battery unit (1010) to handle assembly (1014) and shaft assembly (16), as shown in block (3000). As such, switch arm (1046) directs discharge switch (1070) from the blocker position to the released position, and discharge cathode contact (1060) moves from the open position to the closed position to connect batteries (1028) to drain circuit (1152). After operative connection, surgical instrument (1000) may rest or be generally handled by the user without initiating timer (1182*a*). However, once the user directs batteries (1028) to initially discharge electrical power, as shown in block (3002), timer (1128*a*) begins computing the passage of time, as shown in block (3004) until reaching the predetermined amount of time from initial discharge of electrical power. This counting continues as the operator uses instrument (1000) to treat the patient, as shown in block (3006).

Once the predetermined amount of time is computed by timer (1182*a*), timer (1182*a*) sends a discharge signal to MOSFET transistor (1080) via opto-isolator (1182*b*) in order to close drain circuit (1152) with resistor (1078) between cathode and anode (1066, 1068), as shown in block (3008). Closing drain circuit (1152) directs electrical power through resistor (1078), as shown in block (3010), and effectively drains a remaining portion of electrical power from batteries (1028), as shown in block (3012). In other words, drain (1112) delays draining electrical power from battery unit (1010) until the predetermined amount of time has passed. Drained battery unit (1010) may then be properly disposed of, as shown in block (3014).

In the present example, timer (1182*a*) begins to count time (i.e., to determine whether the predetermined duration has passed) after the first time electrical power is discharged from batteries (1028) (e.g., during use of instrument (1000) in a surgical procedure). In some other versions, timer (1182*a*) begins to count time (i.e., to determine whether the predetermined duration has passed) after battery unit (1010) is inserted into battery dock (1018), regardless of when power is first discharged from batteries (1028) (e.g., during use of instrument (1000) in a surgical procedure). Other events that may be relied on to trigger the counting of time by timer (1182*a*) will be apparent to those of ordinary skill in the art in view of the teachings herein.

C. Exemplary Battery Drain Using Sensor

Figure 29:
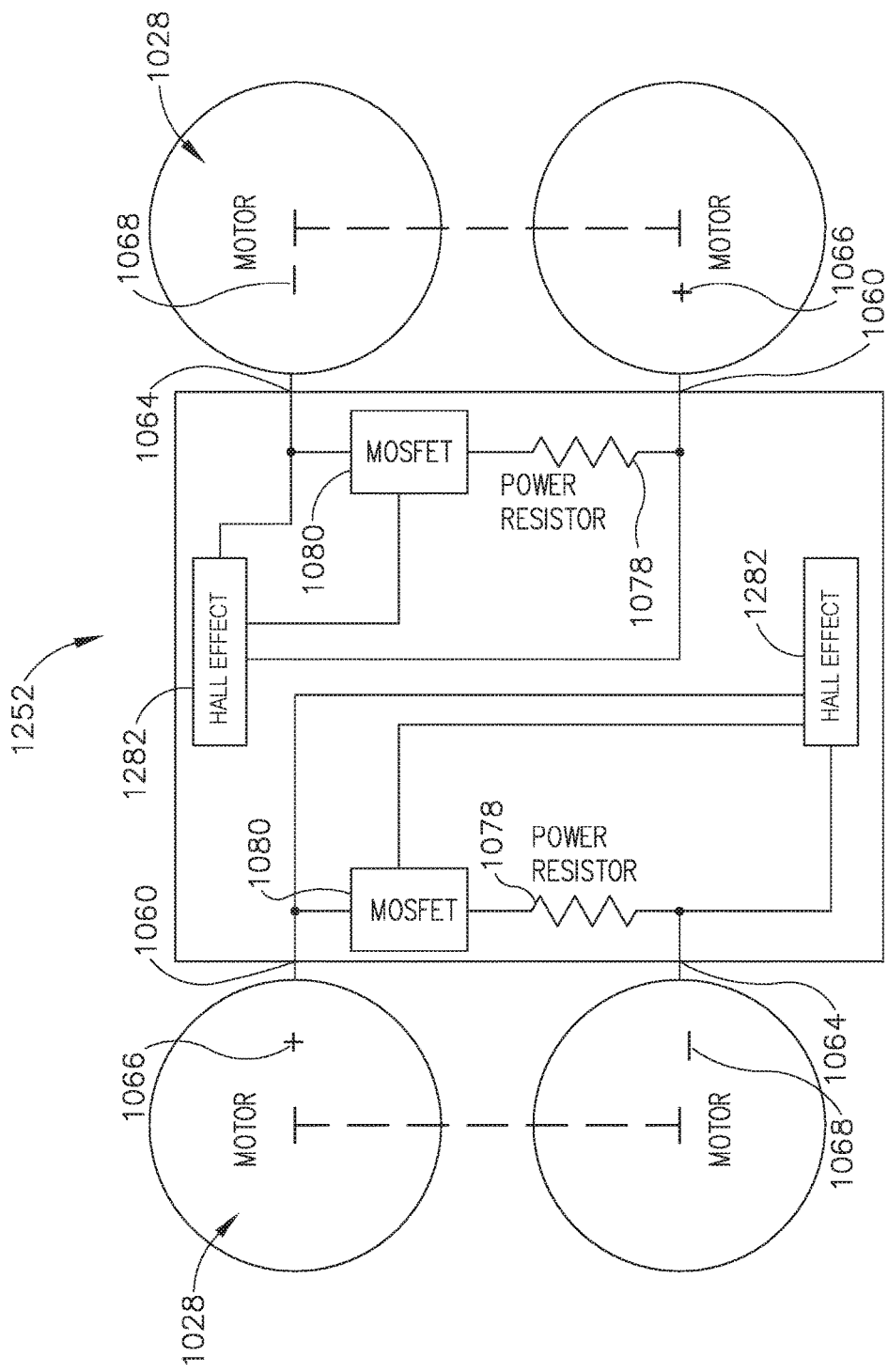
FIG. 29 depicts a schematic circuit diagram of another exemplary alternative power drain circuit.

FIG. 29 shows another exemplary alternative power drain circuit (1252) that may be readily incorporated into instrument (1000) in place of power drain circuit (1052) described above. In particular, FIG. 29 schematically shows power drain circuit (1252) of drain (1212) with discharge circuit board (1272) for delaying and initiating drain of batteries (1028). Power drain circuit (1252) further includes a resistor element, such as a resistor (1078); a switch element, such as a metal-oxide semiconductor field-effect ("MOSFET") transistor (1080); and a controller, such as the Hall effect sensor (1282). In the present example, power drain circuit (1252) is configured to delay draining electrical power across resistor (1078) until battery unit (1010) is removed from battery dock (1018).

With respect to the controller, Hall effect sensor (1282) is configured to sense when battery unit (1010) is removed from battery dock (1018) and communicate the sensed removal directly to MOSFET transistor (1080). It will be appreciated that various structures, mechanical, electrical, and magnetic, may be used to communicate removal to microprocessor (1082*a*). For example, battery dock (1018) may include a pair of magnets (not shown) in proximity to each Hall effect sensor (1282) such that a reduction in magnetic field upon removal of Hall effect sensor (1282) from battery dock (1018) causes Hall effect sensor (1282) to communicate this removal to MOSFET transistor (1080). Given alternative methods for sensing removal with a portion (1282) of controller, alternative sensors may be so used. In addition, the Hall effect sensor (1082*b*) may alternatively be any form of proximity sensor, such as a reed switch microswitch, configured to sense removal thereof.

Hall effect sensor (1282) is directly connected to MOSFET transistor (1080), which acts as a switch that is configured to selectively electrically connect cathode (1066) to anode (1068) across resistor (1078). Prior to receiving the discharge signal, MOSFET transistor (1080) maintains an open circuit across resistor (1078) to prevent electrical power from cathode (1066) from flowing through resistor (1078). After receiving the discharge signal from Hall effect sensor (1282), MOSFET transistor (1080) closes the circuit across resistor (1078) to direct electrical power from cathode (1066) through resistor (1078) and effectively drain batteries (1028) across resistor (1078). Thereby, draining of batteries (1028) by power drain circuit (1252) is delayed until removal of battery unit (1010). FIG. 29 shows two such power drain circuits (1252) for two sets of batteries (1028). However, it will be appreciated that more or less power drain circuits (1252) may be so used for draining the batteries (1028).

Figure 30:
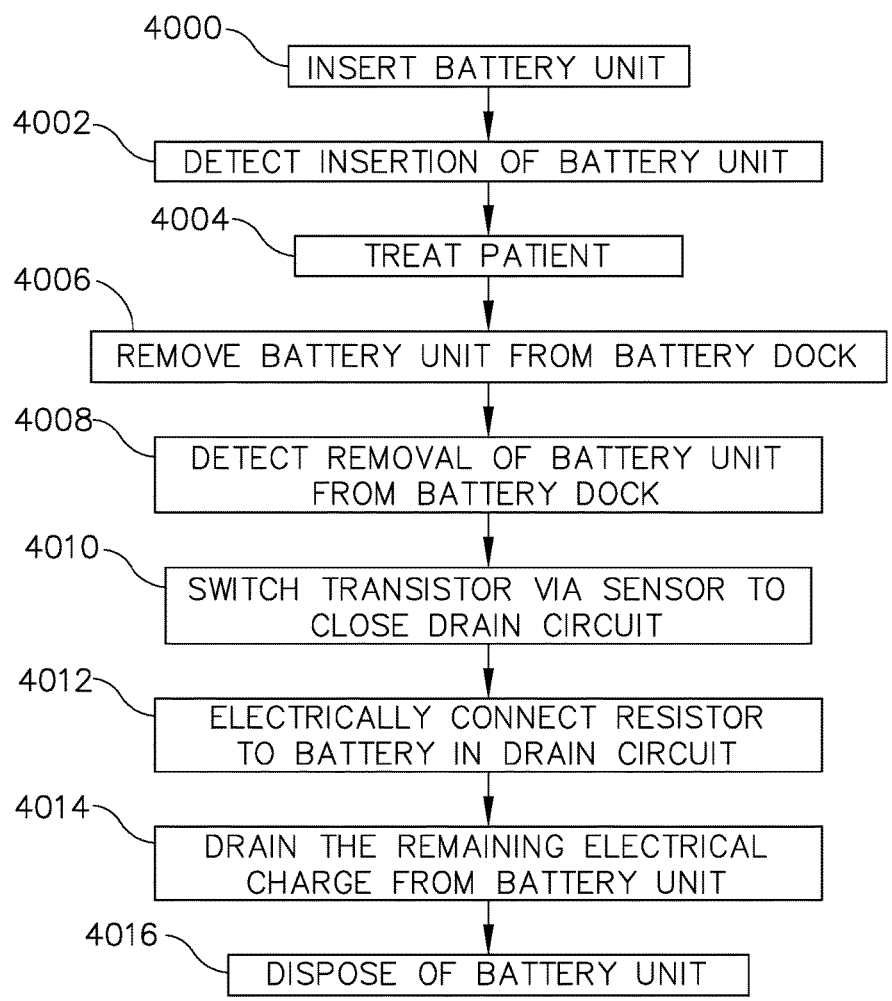
FIG. 30 depicts a flow chart showing an exemplary use of the power drain circuit of FIG. 29 with a surgical instrument.

FIG. 30 shows a flow chart of an exemplary use of surgical instrument (1000) having drain circuit (1252) in relation to FIGS. 16-17, 21, and 29-30. The user inserts battery unit (1010) into battery dock (1018) to operatively connect battery unit (1010) to handle assembly (1014) and shaft assembly (16), as shown in block (4000). As such, switch arm (1046) directs discharge switch (1070) from the blocker position to the released position, and discharge cathode contact (1060) moves from the open position to the closed position to connect batteries (1028) to power drain circuit (1252). Power drain circuit (1252) thus detects insertion of battery unit (1010) into battery dock (1018), as shown in block (4002). The operator then uses instrument (1000) to treat the patient, as shown in block (4004). In this example, power drain circuit (1252) does not drain batteries (1028) during the surgical procedure, even if the surgical procedure extends over a significant period of time, so long as battery unit (1010) remains disposed in battery dock (1018).

After treatment, the operator removes battery unit (1010) from battery dock (1018), as shown in block (4006). Hall effector sensor (1282) detects removal of battery unit (1010) from battery dock (1018), as shown in block (4008); and sends the discharge signal directly to MOSFET transistor (1080), as shown in block (4010), in order to close drain circuit (1252) with resistor (1078) between cathode and anode (1066, 1068), as shown in block (4012). Closing drain circuit (1252) directs electrical power through resistor (1078) and effectively drains a remaining portion of electrical power from batteries (1028), as shown in block (4014). In other words, drain (1212) delays draining electrical power from battery unit (1010) until battery unit (1010) is removed from battery dock (1018). Drained battery unit (1010) may then be properly disposed of, as shown in block (4016).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly having a distal end portion and a proximal end portion, the distal end portion including an end effector projecting distally therefrom; (b) a handle assembly configured to receive the proximal end portion of the shaft assembly, wherein the handle assembly includes a battery dock; and (c) a battery unit configured to be received by the battery dock such that the battery unit is in electrical communication with at least one of the shaft assembly or the handle assembly, the battery unit including: (i) a battery, wherein the battery comprises: (A) an anode contact, and (B) a cathode contact, and (ii) a discharge drain including: (A) a controller, and (B) a battery power draining element, wherein the controller is configured to selectively place the battery power draining element in communication with the anode and cathode contacts to thereby drain power from the battery in response to either coupling of the battery unit with the battery dock or removal of the battery unit from the battery dock.

Example 2

The surgical instrument of Example 1, wherein the controller is configured to sense detachment of the battery unit from the battery dock such that the controller element is configured to selectively place the battery power draining element in communication with the anode and cathode contacts to thereby drain power from the battery in response to removal of the battery unit from the battery dock.

Example 3

The surgical instrument of Example 2, wherein the controller includes a microprocessor configured to receive a signal indicating that the battery unit has been detached from the battery dock.

Example 4

The surgical instrument of Example 3, wherein the controller includes a Hall effect sensor configured to sense when the battery unit has been detached from the battery dock, wherein the hall effect sensor is further configured to send the signal to the microprocessor.

Example 5

The surgical instrument of any one or more of Examples 1 through 4, wherein the discharge drain further comprises a switch element in communication with the controller and the battery power draining element, wherein the switch element is operable to selectively close to thereby place the battery power draining element in communication with the anode and cathode contacts to thereby drain power from the battery.

Example 6

The surgical instrument of Example 5, wherein the switch element comprises a MOSFET transistor.

Example 7

The surgical instrument of Example 6, wherein the controller includes a microprocessor and an opto-isolator in electrical communication between the MOSFET transistor and the microprocessor, wherein the opto-isolator is configured to transfer the signal from the microprocessor to the MOSFET transistor.

Example 8

The surgical instrument of any one or more of Examples 1 through 7, wherein the battery power draining element comprises a resistor.

Example 9

The surgical instrument of any one or more of Examples 1 through 8, wherein the controller includes a timer, wherein the timer is configured to sense attachment of the battery unit to the battery dock and responsively begin tracking, wherein the timer is further configured to selectively place the battery power draining element in communication with the anode and cathode contacts to thereby drain power from the battery after a predetermined amount of time has elapsed since the attachment of the battery unit to the battery dock.

Example 10

The surgical instrument of Example 9, wherein the timer is configured to continue tracking time during and after use of the end effector in a surgical procedure.

Example 11

The surgical instrument of any one or more of Examples 1 through 10, wherein the discharge drain further includes a discharge contact configured to selectively move from an open position to a closed position in response to attachment of the battery unit to the battery dock, wherein at least one of the anode contact and the cathode contact is electrically disconnected from the discharge drain in the open position, and wherein each of the anode contact and the cathode contact is electrically connected to the discharge drain in the closed position.

Example 12

The surgical instrument of Example 11, wherein the discharge contact is biased toward the closed position and the battery power draining element includes a discharge switch configured to selectively move from a blocker position to a released position, wherein the discharge switch is configured to hold the discharge contact in the open position before the battery unit is attached to the battery dock, and wherein the discharge switch is configured to release the discharge contact to the closed position in response to attachment of the battery unit to the battery dock.

Example 13

The surgical instrument of Example 12, wherein the battery unit has a base detent and the discharge switch has a corresponding switch detent, wherein the base and switch detents are configured to cooperatively secure the discharge switch in the released position.

Example 14

The surgical instrument of Example 13, wherein the battery dock includes a protruding member extending therein, wherein the protruding member is configured to engage the discharge switch and move the discharge switch from the blocker position to the released position upon attaching the battery unit to the battery dock.

Example 15

The surgical instrument of any one or more of Examples 1 through 14, wherein the end effector is operable to cut tissue and apply staples to tissue.

Example 16

The surgical instrument of any one or more of Examples 1 through 15, wherein the shaft assembly is selectively removable from the handle assembly.

Example 17

A surgical instrument, comprising: (a) a shaft assembly having a distal end portion and a proximal end portion, the distal end portion including an end effector projecting distally therefrom; (b) a handle assembly configured to receive the proximal end portion of the shaft assembly, wherein the handle assembly includes a battery dock; and (c) a battery unit configured to be received by the battery dock such that the battery unit is in electrical communication with at least one of the shaft assembly or the handle assembly, the battery unit including: (i) a casing; (ii) an anode contact and a cathode contact positioned within the casing and configured to electrically connect to at least one battery; and (iii) a discharge drain including a discharge contact and a controller configured to sense a predetermined input, wherein the discharge contact is configured to selectively move from an open position to a closed position in response to attachment of the battery unit to the battery dock, wherein at least one of the anode contact and the cathode contact is electrically disconnected from the discharge drain in the open position, wherein each of the anode contact and the cathode contact is electrically connected to the discharge drain in the closed position, and wherein the controller is configured drain a remaining electrical power from the at least one battery connected to the anode contact and the cathode contact only upon sensing the predetermined input.

Example 18

The surgical instrument of Example 17, wherein the controller is configured to sense detachment of the battery unit from the battery dock as the predetermined input.

Example 19

The surgical instrument of any one or more of Examples 17 through 18, wherein the controller includes a timer configured to compute a predetermined amount of time, wherein the controller configured to sense discharge of an electrical power from the at least one battery such that the timer will initiate computation of the predetermined amount of time from the discharge of the electrical power, wherein the passage of the predetermined amount of time is the predetermined input.

Example 20

A method of discharging a remaining electrical power from at least one battery of a surgical instrument, the surgical instrument including a handle assembly, a shaft assembly extending distally from the handle assembly, an end effector located at a distal end of the shaft assembly, and a battery unit, wherein the battery unit includes at least one battery and a discharge drain, wherein the handle assembly includes a battery dock configured to receive the battery unit such that the battery unit is in electrical communication with at least one of the shaft assembly or the handle assembly, the method comprising: (a) discharging an electrical power from the at least one battery to at least one of the handle assembly or the shaft assembly; (b) detaching the battery unit from the battery dock; (c) sensing the act of detaching the battery unit from the battery dock; (d) coupling the at least one battery with the discharge drain in response to sensing the act of detaching the battery unit from the battery dock; and (e) draining a remaining power from the at least one battery via the discharge drain while the battery unit remains detached from the battery dock.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a shaft assembly having a distal end portion and a proximal end portion, the distal end portion including an end effector projecting distally therefrom;
   (b) a handle assembly configured to receive the proximal end portion of the shaft assembly, wherein the handle assembly includes a battery dock; and
   (c) a battery unit configured to be received by the battery dock such that the battery unit is in electrical communication with at least one of the shaft assembly or the handle assembly, the battery unit including:
      (i) a battery, wherein the battery comprises:
         (A) an anode contact, and
         (B) a cathode contact, and
      (ii) a discharge drain including:
         (A) a controller including a sensor and a microprocessor, wherein the sensor is configured to sense when the battery unit has been detached from the battery dock and send a signal to the microprocessor indicating that the battery unit has been detached from the battery dock, and
         (B) a battery power draining element, wherein the controller is configured to selectively place the battery power draining element in communication with the anode and cathode contacts to thereby drain power from the battery in response to removal of the battery unit from the battery dock.

2. The surgical instrument of claim 1, wherein the controller is configured to sense detachment of the battery unit from the battery dock such that the controller element is configured to selectively place the battery power draining element in communication with the anode and cathode contacts to thereby drain power from the battery in response to removal of the battery unit from the battery dock.

3. The surgical instrument of claim 1, wherein the sensor is a includes a Hall effect sensor.

4. The surgical instrument of claim 1, wherein the discharge drain further comprises a switch element in communication with the controller and the battery power draining element, wherein the switch element is operable to selectively close to thereby place the battery power draining element in communication with the anode and cathode contacts to thereby drain power from the battery.

5. The surgical instrument of claim 4, wherein the switch element comprises a MOSFET transistor.

6. The surgical instrument of claim 5, wherein the controller includes a microprocessor and an opto-isolator in electrical communication between the MOSFET transistor and the microprocessor, wherein the opto-isolator is configured to transfer the signal from the microprocessor to the MOSFET transistor.

7. The surgical instrument of claim 5, wherein the battery dock includes a magnet in proximity to the sensor such that a reduction in magnetic field upon removal of the sensor from the battery dock is configured to cause the sensor to communicate the removal to MOSFET transistor.

8. The surgical instrument of claim 1, wherein the battery power draining element comprises a resistor.

9. The surgical instrument of claim 1, wherein the controller includes a timer, wherein the timer is configured to sense attachment of the battery unit to the battery dock and responsively begin tracking, wherein the timer is further configured to selectively place the battery power draining element in communication with the anode and cathode contacts to thereby drain power from the battery after a predetermined amount of time has elapsed since the attachment of the battery unit to the battery dock.

10. The surgical instrument of claim 9, wherein the timer is configured to continue tracking time during and after use of the end effector in a surgical procedure.

11. The surgical instrument of claim 1, wherein the discharge drain further includes a discharge contact configured to selectively move from an open position to a closed position in response to attachment of the battery unit to the battery dock, wherein at least one of the anode contact and the cathode contact is electrically disconnected from the discharge drain in the open position, and wherein each of the anode contact and the cathode contact is electrically connected to the discharge drain in the closed position.

12. The surgical instrument of claim 11, wherein the discharge contact is biased toward the closed position and the battery power draining element includes a discharge switch configured to selectively move from a blocker position to a released position, wherein the discharge switch is configured to hold the discharge contact in the open position before the battery unit is attached to the battery dock, and wherein the discharge switch is configured to release the discharge contact to the closed position in response to attachment of the battery unit to the battery dock.

13. The surgical instrument of claim 12, wherein the battery unit has a base detent and the discharge switch has a corresponding switch detent, wherein the base and switch detents are configured to cooperatively secure the discharge switch in the released position.

14. The surgical instrument of claim 13, wherein the battery dock includes a protruding member extending therein, wherein the protruding member is configured to engage the discharge switch and move the discharge switch from the blocker position to the released position upon attaching the battery unit to the battery dock.

15. The surgical instrument of claim 1, wherein the end effector is operable to cut tissue and apply staples to tissue.

16. The surgical instrument of claim 1, wherein the shaft assembly is selectively removable from the handle assembly.

17. The surgical instrument of claim 1, wherein the discharge drain is configured to not drain the battery unit during a surgical procedure so long as the battery unit remains disposed in the battery dock.

18. A surgical instrument, comprising:
 (a) a shaft assembly having a distal end portion and a proximal end portion, the distal end portion including an end effector projecting distally, therefrom;
 (b) a handle assembly configured to receive the proximal end portion of the shaft assembly, wherein the handle assembly includes a battery dock; and
 (c) a battery unit configured to be received by the battery dock such that the battery unit is in electrical communication with at least one of the shaft assembly or the handle assembly, the battery unit including:
  (i) a casing;
  (ii) an anode contact and a cathode contact positioned within the casing and configured to electrically connect to at least one battery; and
  (iii) a discharge drain including:
   (A) a discharge contact configured to selectively move from an open position to a closed position, wherein at least one of the anode contact and the cathode contact is electrically disconnected from the discharge drain in the open position, and wherein each of the anode contact and the cathode contact is electrically connected to the discharge drain in the closed position, and
   (B) a controller configured to sense an initial discharge of the battery unit, wherein the controller includes a timer configured to delay draining any remaining electrical power from the at least one battery connected to the anode contact and the cathode contact until the predetermined amount of time has elapsed after the initial discharge of the battery unit.

19. The surgical instrument of claim 18, wherein the controller is configured to sense detachment of the battery unit from the battery dock.

20. A method of discharging a remaining electrical power from at least one battery of a surgical instrument, the surgical instrument including a handle assembly, a shaft assembly extending distally from the handle assembly, an end effector located at a distal end of the shaft assembly, and a battery unit, wherein the battery unit includes at least one battery and a discharge drain, wherein the handle assembly includes a battery dock configured to receive the battery unit such that the battery unit is in electrical communication with at least one of the shaft assembly or the handle assembly, the method comprising:
 (a) discharging an electrical power from the at least one battery to at least one of the handle assembly or the shaft assembly;
 (b) detaching the battery unit from the battery dock;
 (c) sensing the act of detaching the battery unit from the battery dock using a sensor that produces a signal;
 (d) sending the signal from the sensor to a microprocessor indicating that the battery unit has been detached from the battery dock;
 (e) coupling the at least one battery with the discharge drain in response to sensing the act of detaching the battery unit from the battery dock; and
 (f) draining a remaining power from the at least one battery via the discharge drain while the battery unit remains detached from the battery dock.

* * * * *